US008232241B2

(12) United States Patent
Larusso et al.

(10) Patent No.: US 8,232,241 B2
(45) Date of Patent: Jul. 31, 2012

(54) TREATING LIVER DISEASES

(75) Inventors: Nicholas F. Larusso, Rochester, MN (US); Tetyana V. Masyuk, Rochester, MN (US); Melissa Muff-Luett, Minneapolis, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 931 days.

(21) Appl. No.: 11/915,107

(22) PCT Filed: May 1, 2006

(86) PCT No.: PCT/US2006/016623
§ 371 (c)(1),
(2), (4) Date: Jul. 7, 2008

(87) PCT Pub. No.: WO2006/127214
PCT Pub. Date: Nov. 30, 2006

(65) Prior Publication Data
US 2009/0170754 A1 Jul. 2, 2009

Related U.S. Application Data

(60) Provisional application No. 60/683,617, filed on May 23, 2005.

(51) Int. Cl.
*A61K 38/12* (2006.01)
(52) U.S. Cl. .......................................... 514/1.1; 435/375
(58) Field of Classification Search .................. None
See application file for complete search history.

(56) References Cited

U.S. PATENT DOCUMENTS 5,583,104 A * 12/1996 LaRusso ................. 514/11.1

OTHER PUBLICATIONS

Chauveau et al., "Liver Involvement in Autosomal-Dominant Polycystic Kidney Disease: Therapeutic Dilemma," *J. Am. Soc. Nephrol.*, 2000, 11:1767-1775.
Drenth et al., "Molecular Characterization of Hepatocystin, the Protein That Is Defective in Autosomal Dominant Polycystic Liver Disease," *Gastroenterology*, 2004, 126:1819-1827.

Drenth et al., "Germline mutations in *PRKCSH* are associated with autosomal dominant polycystic liver disease," *Nat. Genet.*, 2003, 33:345-347.
Everson et al., "Polycystic Disease of the Liver," *Hepatology*, 2004, 40:774-782.
Froidevaux and Eberle, "Somatostatin Analogs and Radiopeptides in Cancer Therapy," *Biopolymers*, 2002, 66:161-83.
Harris and Rossetti, "Molecular genetics of autosomal recessive polycystic kidney disease," *Molecular Genetics and Metabolism*, 2004, 81:75-85.
Iglesias et al., "Isolated Polycystic Liver Disease Not Linked to Polycystic Didney Disease 1 and 2," *Dig. Dis. Sci.*, 1999, 44(2):385-388.
Masyuk et al., "Defects in Cholangiocyte Fibrocystin Expression and Ciliary Structure in the PCK Rat," *Gastroenterology*, 2003, 125:1303-1310.
Masyuk et al., "Biliary dysgenesis in the PCK rat, an orthologous model of autosomal recessive polycystic kidney disease," *Am. J. Pathol.*, 2004, 165:1719-1730.
Qian et al., "Clinical profile of autosomal dominant polycystic liver disease," *Hepatology*, 2003,.37:164-171.
Roberts et al., "Regulation of bicarbonate-dependent ductular bile secretion assessed by lumenal micropuncture of isolated rodent intrahepatic bile ducts," Proc. Natl. Acad. Sci. USA, 1993,90:9080-9084.
Reynolds et al., "Identification of a Locus for Autosomal Dominant Polycystic Liver Disease, on Chromosome 19p13.2-13.1," *Am. J. Hum. Genet.*, 2000, 67:1598-1604.
Ruggenenti et al., "Safety and efficacy of long-acting somatostatin treatment in autosomal-dominant polycystic kidney disease," *Kidney Int.*, 2005, 68:206-216.
Sherlok, *Schiff's Diseases of the Liver*, 1999, pp. 1083-1090.
Ward et al., "The gene mutated in autosomal recessive polycystic kidney disease encodes a large, receptor-like protein," *Nat. Genet.*, 2002, 30:259-269.
Wang et al., "Effectiveness of Vasopressin V2 Receptor Antagonists OPC-31260 and OPC-41061 on Polycystic Kidney Disease Development in PCK Rat," *J. Am. Soc. Nephrol.*, 2005, 16:846-851.
Masyuk et al., "Octreotide inhibits hepatic cystogenesis in a rodent model of polycystic liver disease by reducing cholangiocyte adenosine 3', 5'-cyclic monophosphate," *Gastroenterology*, 2007, 132: 1104-1116.
Supplementary European Search Report from EP 06 75 2001, dated Mar. 14, 2012, 7 pages.

* cited by examiner

*Primary Examiner* — Karlheinz R Skowronek
*Assistant Examiner* — Roy Teller
(74) *Attorney, Agent, or Firm* — Fish & Richardson P.C.

(57) ABSTRACT

This document provides methods and materials related to treating liver conditions. For example, the methods and materials relating to the use of cAMP inhibitors to treat liver conditions are provided.

17 Claims, 18 Drawing Sheets

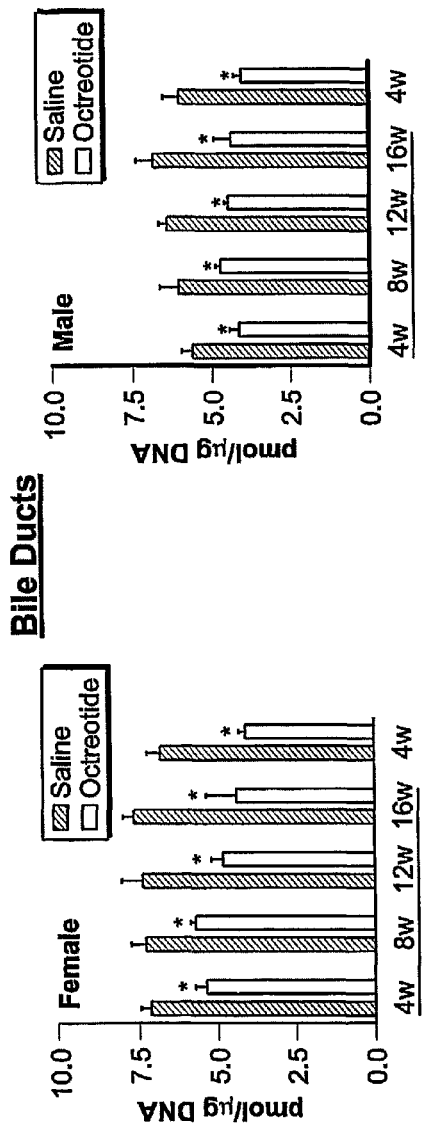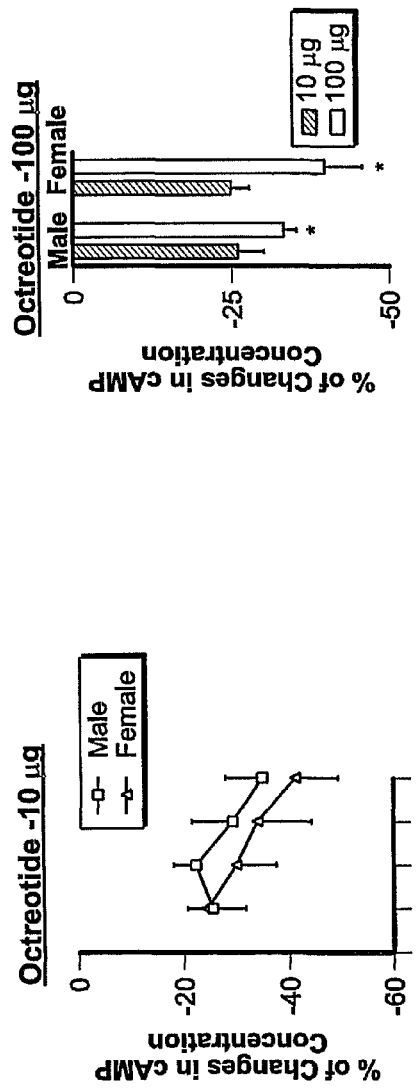

US 8,232,241 B2

TREATING LIVER DISEASES

CROSS-REFERENCE TO RELATED APPLICATIONS

This application is a National Stage application under 35 U.S.C. §371 and claims benefit under 35 U.S.C. §119(a) of International Application No. PCT/US2006/016623 having an International Filing Date of May 1, 2006, which claims the benefit of U.S. Provisional Application Serial No. 60/683,617, having a filing date of May 23, 2005.

STATEMENT AS TO FEDERALLY SPONSORED RESEARCH

This invention was made with government support under DK024031 awarded by the National Institute of Diabetes and Digestive and Kidney Diseases. The government has certain rights in the invention.

BACKGROUND

1. Technical Field

This document relates to methods and materials involved in treating liver conditions such as hepatic polycystic disease.

2. Background Information

Hepatic polycystic disease is genetically heterogeneous and occurs alone or in combination with polycystic kidney disease. Autosomal dominant polycystic liver disease (AD-PLD) displays no renal involvement and is caused by mutation of two genes: PRKCSH (protein kinase substrate 80K-H) on chromosome 19p13 that encodes the protein hepatocystin and sec63 (endothelial reticulum translocon component (*S. cerevisiae*) like) located on chromosome 6q21. ADPLD is characterized by an overgrowth of the biliary epithelium and supportive connective tissue. Hepatic cysts are more prominent in women and dramatically increase in number and size during the child-bearing years (Everson et al., *Hepatology*, 40:774-782 (2004); Drenth et al., *Gastroenterology*, 126: 1819-1827 (2004); Reynolds et al., *Am. J Hum. Genet.*, 67:1598-1604 (2000); Qian et al., *Hepatology*, 37:164-171 (2003); Iglesias et al., *Dig. Dis. Sci.*, 44: 385-388 (1999); and Drenth et al., *Nat. Genet.*, 33:345-347 (2003)).

SUMMARY

This document provides methods and materials related to treating liver conditions. Typically, a liver condition can be a liver condition characterized by the presence of solitary or multiple liver cysts that can result from abnormal cell growth and fluid secretion. For example, the methods and materials provided herein can be used to treat liver conditions that involve the presence of one or more cysts. In some embodiments, the methods and materials provided herein can be used to reduce the size or number of cysts within liver tissue. Reducing the size or number of cysts within liver tissue can allow patients to live longer and healthier lives.

This document is based, in part, on the discovery that the growth and expansion of liver cysts can be slowed or stopped by treating liver tissue with a cAMP inhibitor. For example, somatostatin can be used to inhibit liver cyst growth and expansion.

In general, this document features a method for inhibiting cyst growth. The method includes (a) identifying liver tissue containing a liver cyst, and (b) contacting the liver cyst with a cAMP inhibitor under conditions wherein the growth rate of the liver cyst is reduced as compared to the growth rate of a comparable liver cyst not contacted with the cAMP inhibitor. The identifying step can include imaging the liver tissue using ultrasonography, CT scans, or magnetic resonance imagery. The liver tissue can be human liver tissue. The contacting step can include administering the cAMP inhibitor to a mammal containing the liver tissue. The method can include administering the cAMP inhibitor to the mammal on an at least daily basis. The method can include administering the cAMP inhibitor to the mammal on an at least weekly basis. The method call include administering the cAMP inhibitor to the mammal on an at least monthly basis. The method can include orally administering the cAMP inhibitor to the mammal. The method can include injecting the cAMP inhibitor into the mammal. The cAMP inhibitor can be somatostatin, octreotide, lanreotide, vapreotide, or any other somatostatin analog, ursodeoxycholic acid, taurourso-deoxycholic acid, or gastrin. The cAMP inhibitor can be formulated as a slow-release cAMP inhibitor. The cAMP inhibitor can be formulated as a long-lasting cAMP inhibitor or as a short-acting cAMP inhibitor. The method can include contacting the liver cyst with two or more of the cAMP inhibitors. The method can include detecting a reduced growth rate of the liver cyst following the contacting step.

In another embodiment, this document features a method for inhibiting cyst growth. The method includes (a) identifying liver tissue containing a liver cyst having a growth rate, and (b) contacting the liver cyst with a cAMP inhibitor under conditions wherein the growth rate of the liver cyst is reduced. The identifying step can include imaging the liver tissue using ultrasonography, CT scans, or magnetic resonance imagery. The liver tissue can be human liver tissue. The contacting step can include administering the cAMP inhibitor to a mammal containing the liver tissue. The method can include administering the cAMP inhibitor to the mammal on an at least daily basis. The method can include administering the cAMP inhibitor to the mammal on an at least weekly basis. The method can include administering the cAMP inhibitor to the mammal on an at least monthly basis. The method can include orally administering the cAMP inhibitor to the mammal. The method can include injecting the cAMP inhibitor into the mammal. The cAMP inhibitor can be somatostatin, octreotide, lanreotide, vapreotide, or any other somatostatin analog, ursodeoxycholic acid, tauroursodeoxycholic acid, or gastrin. The cAMP inhibitor can be formulated as a slow-release cAMP inhibitor. The cAMP inhibitor can be formulated as a long-lasting cAMP inhibitor or as a short-acting cAMP inhibitor. The method can include contacting the liver cyst with two or more of the cAMP inhibitors. The method can include detecting a reduced growth rate of the liver cyst following the contacting step.

In another embodiment, this document features a method for inhibiting cyst growth in a mammal. The method includes (a) identifying the mammal as having liver tissue containing a liver cyst, wherein the liver cyst has a size, and (b) administering a cAMP inhibitor to the mammal in an amount and at a frequency effective to prevent the size from increasing more than 100 percent within a two month time period. The identifying step can include imaging liver tissue of the mammal using ultrasonography, CT scans, or magnetic resonance imagery. The mammal can be a human. The frequency can be at least daily. The frequency can be at least weekly. The frequency can be at least monthly. The administering step can include orally administering the cAMP inhibitor to the mammal. The administering step can include injecting the cAMP inhibitor into the mammal. The cAMP inhibitor can be somatostatin, octreotide, lanreotide, vapreotide, or any other somatostatin analog, ursodeoxycholic acid, tauroursodeoxycholic acid, or gastrin. The cAMP inhibitor can be formulated as a slow-release cAMP inhibitor. The cAMP inhibitor can be formulated as a long-lasting cAMP inhibitor or as a short-acting cAMP inhibitor. The method can include administering two or more of the cAMP inhibitors to the mammal. The administering step can be effective to prevent the size from increasing more than 50 percent within a six month time period. The administering step can be effective to prevent the size from increasing more than 25 percent within a six month time period. The administering step can be effective to prevent the size from increasing more than 100 percent within a 12 month time period. The method can include determining whether the size increased more than 100 percent within a 36 month time period.

In another embodiment, this document features a method for reducing liver volume. The method comprises, or consists essentially of, (a) identifying a liver comprising a liver cyst, and (b) contacting the liver with a cAMP inhibitor under conditions where the volume of the liver is reduced as compared to the volume of a comparable liver not contacted with the cAMP inhibitor.

In another embodiment, this document features a method for inhibiting cyst growth. The method comprises, or consists essentially of, (a) identifying kidney tissue comprising a kidney cyst, and (b) contacting the kidney cyst with a cAMP inhibitor under conditions where the growth rate of the kidney cyst is reduced as compared to the growth rate of a comparable kidney cyst not contacted with the cAMP inhibitor.

In another embodiment, this document features a method for inhibiting cyst growth. The method comprises, or consists essentially of, (a) identifying kidney tissue comprising a kidney cyst having a growth rate, and (b) contacting the kidney cyst with a cAMP inhibitor under conditions where the growth rate of the kidney cyst is reduced.

In another embodiment, this document features a method for inhibiting cyst growth in a mammal. The method comprises, or consists essentially of, (a) identifying the mammal as having kidney tissue comprising a kidney cyst, where the kidney cyst has a size, and (b) administering a cAMP inhibitor to the mammal in an amount and at a frequency effective to prevent the size from increasing more than 100 percent within a two month time period.

In another embodiment, this document features a method for inhibiting kidney or liver fibrosis. The method comprises, or consists essentially of, (a) identifying kidney or liver tissue comprising kidney or liver fibrosis, and (b) contacting the kidney or liver tissue with a cAMP inhibitor under conditions where the fibrosis is reduced as compared to the fibrosis of comparable kidney or liver tissue not contacted with the cAMP inhibitor.

In another embodiment, this document features a method for inhibiting kidney or liver fibrosis. The method comprises, or consists essentially of, (a) identifying kidney or liver tissue comprising fibrosis, and (b) contacting the kidney or liver tissue with a cAMP inhibitor tinder conditions where the fibrosis is reduced.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 13 also contains graphs plotting the percent change in cAMP concentration in bile ducts (panels C-D) and serum (panels G-H) after treatment with saline as compared to treatment with 10 µg/kg of octreotide for 4, 8, 12, or 16 weeks or 100 µg/kg of octreotide for 4 weeks.

FIG. 16 also contains representative photomicrographs (magnification ×4) of liver tissues from the saline- and octreotide-treated groups.

FIG. 17 also contains representative photomicrographs of kidney tissues from the saline- and octreotide-treated groups.

DETAILED DESCRIPTION

Figure 1:
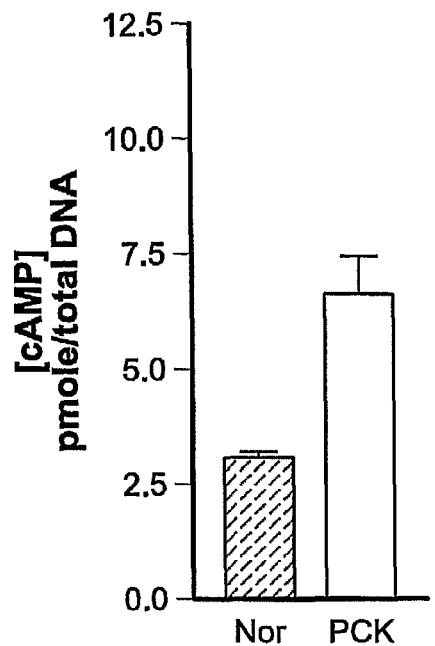
FIG. 1 is a graph plotting cAMP levels measured in bile ducts isolated from normal (Nor) or PCK rats (an animal model of ARPKD characterized by massive cyst formation in liver and kidneys).

This document provides methods and materials related to treating liver conditions. For example, this document provides methods and materials related to the use of cAMP inhibitors to treat liver conditions. The term "liver condition" as used herein refers to the presence of abnormal cell growth in liver tissue. A liver condition can be, without limitation, polycystic liver disease or a condition having the presence of one or more liver cysts. In some cases, the methods and materials provided herein can be used to treat a single liver condition (e.g., a patient with polycystic liver disease) or a combination of liver conditions.

As described herein, a cAMP inhibitor can be used to treat a liver condition. The term "cAMP inhibitor" as used herein refers to any compound having the ability to reduce cAMP levels within a cell. Examples of cAMP inhibitors that can be used as described herein include, without limitation, somatostatin, octreotide, Sandostatin® LAR® (an injectable suspension of octreatide acetate that is a long-lasting formulation), lanreotide, Somatuline® SR® (a slow-release analog of lanreotide), vapreotide, or any other somatostatin analog, ursodeoxycholic acid (e.g., ursodiol or UDCA), tauroursodeoxycholic acid (TUDCA), and gastrin.

In general, liver conditions can be treated by contacting liver cells (e.g., a liver cyst) with a cAMP inhibitor. Any method can be used to contact liver cells with a compound such as a cAMP inhibitor. For example, cAMP inhibitors can be administered orally or via injection (e.g., intramuscular injection, intravenous injection, or intracyst injection) so that the administered cAMP inhibitor contacts liver cells.

Before administering a cAMP inhibitor to a mammal, the mammal can be assessed to determine whether or not the mammal has a liver condition. Any method can be used to determine whether or not a mammal has a liver condition. For example, a mammal (e.g., human) can be identified as having a liver condition by palpation or upon examination of a tissue biopsy as well as by endoscopic analysis or image analysis techniques (e.g., ultrasonography, CT scans, and magnetic resonance imagery (MRI) scans) since abnormal cell growth and expansion tend to exhibit observable abnormal characteristics. In addition, diagnostic methods such as reviewing an individual's prior medical conditions and treatments, interviewing and evaluating an individual, and collecting and analyzing biological samples from an individual can be used to identify the presence of a liver condition. Typically, clinical symptoms or complications can be assessed to determine whether or not a mammal has a liver condition. For example, a mammal can be diagnosed as having polycystic liver disease based on the presence of symptoms or complications including, without limitation, cystic changes in the liver (characterized, for example, by dilatation of the bile ducts); abdominal distension; fullness; back pain; clinical signs of hepatic fibrosis; cyst infection, hemorrhage, and rupture; portal hypertension; and jaundice (Everson et al., *Hepatology.*, 40:774-782 (2004); Qian et al., *Hepatology*, 37:164-171 (2003); and Chauveau et al., *J. Am. Soc. Nephrol.*, 11:1767-1775 (2000)). Patients with a positive family history can be further evaluated through gene-linkage analysis (Harris et al., *Molecular genetics and metabolism*, 81:75-85 (2004)).

Reviewing an individual's medical history as well as interviewing and evaluating an individual can be helpful in determining the presence of a liver condition since symptoms of liver conditions such as polycystic liver disease include abdominal distension, fullness, back pain, portal hypertension, hepatic fibrosis, and jaundice. Collecting and analyzing biological samples from an individual also can help identify a liver condition. Many methods for detecting the presence of these various signs and markers within a biological sample are well known in the art and can be used. For example, biological samples such as blood or urea can be collected and analyzed for signs that indicate liver dysfunction. While a liver function test can be normal, a significant elevation of gamma-glutamyl transpeptidase (GGT) activity and serum alkaline phosphatase can be detected and used as a marker for a liver condition (Sherlok, In: Schiff's Diseases of the Liver, pp. 1083-1090 (1999); Everson et al., *Heptology*, 40:774-782 (2004)).

In some cases, a tissue biopsy can be collected and analyzed to determine whether or not a mammal has a liver condition. For example, the presence of cells consistent with a cyst morphology found within a liver tissue biopsy can indicate that the mammal has a liver condition. In some cases, immuno-based assays can be used to detect the presence of one or more signs of a liver condition within a biological sample such as a liver tissue biopsy. Many immuno-based assays are well known in the art including, without limitation, enzyme linked immunosorbent assays (ELISA). Immuno-based assays can use polyclonal antibodies, monoclonal antibodies, or fragments thereof that have high binding affinity for a marker indicative of a liver condition. For example, monoclonal or polyclonal antibodies having specificity for hepatocystin, fibrocystin, polycystin 1, or polycystin 2 can be produced and used to screen biological samples. Such antibodies can be produced using methods described elsewhere (Zeidan et al., Experimental Approaches in Biochemistry and Molecular Biology, William C. Brown Publisher (1996) and Seaver, Commercial Production of Monoclonal Antibodies: A Guide for Scale Up, Marcel Dekker Inc., New York, N.Y. (1987)).

After identifying a mammal as having a liver condition, the mammal can be treated with a cAMP inhibitor. A cAMP inhibitor can be administered to a mammal in any amount, at any frequency, and for any duration effective to achieve a desired outcome (e.g., to treat a liver condition). In some cases, a cAMP inhibitor can be administered to a mammal to reduce the growth rate of a liver cyst. The reduction can be any level of reduction including, a 5, 10, 25, 50, 75, 100, or more percent reduction in growth rate. For example, the growth rate can be reduced such that no additional growth is detected. Any method can be used to determine whether or not the growth rate of liver cysts is reduced. For example, the growth rate of liver cysts can be assessed by imaging liver tissue at different time points and determining the increase in cyst growth during a particular time interval. After treatment with a cAMP inhibitor, the growth rate can be determined again over another time interval. In some cases, the stage of growth of the liver cysts after treatment can be determined and compared to the stage before treatment to determine whether or not the growth rate was reduced.

In some embodiments, a cAMP inhibitor can be administered to a mammal in an amount, at a frequency, and for a duration effective to reduce the growth rate of a liver cyst as compared to the growth rate of a comparable liver cyst not contacted with the cAMP inhibitor. For example, the growth rate of liver cysts within PCK rats treated with a cAMP inhibitor can be compared to the growth rate of liver cysts within PCK rates not treated with the cAMP inhibitor. The reduction can be any level of reduction including, a 5, 10, 25, 50, 75, 100, or more percent reduction in growth rate. For example, the growth rate can be reduced such that no additional growth is detected following treatment with a cAMP inhibitor. In some cases, a cAMP inhibitor can be administered to a mammal in an amount, at a frequency, and for a duration effective to prevent the size of a liver cyst from increasing more than 100 percent (e.g., 100, 90, 80, 70, 60, 50, 40, 30, 20, 10, or 5 percent) within a one, two, three, four, five, six, seven, eight, nine, ten, eleven, twelve month time period. For example, a cAMP inhibitor can be administered to prevent the size of a liver cyst from increasing more than 100 percent within a 2 to 36 month time period.

An effective amount of a cAMP inhibitor or formulation containing a cAMP inhibitor can be any amount that reduces abnormal cell growth or abnormal cell expansion in liver tissue of a mammal without producing significant toxicity to the mammal. Typically, an effective amount can be any amount greater than or equal to about 50 µg provided that that amount does not induce significant toxicity to the mammal upon administration. In some cases, the effective amount can be between 100 and 500 µg. If a particular mammal fails to respond to a particular amount, then the amount can be increased by, for example, ten fold. After receiving this higher concentration, the mammal can be monitored for both responsiveness to the treatment and toxicity symptoms, and adjustments made accordingly. When injected, an effective amount can be between 50 µg and 100 µg. The effective amount can remain constant or can be adjusted as a sliding scale or variable dose depending on the mammal's response to treatment.

To help determine effective amounts of different cAMP inhibitors, it can be useful to refer to an effective amount equivalent based on the effective amount of a common cAMP inhibitor. For example, the administration of 50 mg (e.g., once, twice, or three times daily) of short-acting octreotide (e.g., Sandostatin®) can be an effective amount. The effects produced by this effective amount can be used as a reference point to compare the effects observed for other cAMP inhibitors used at varying concentrations. Once an equivalent effect is observed, then the specific effective amount for that particular cAMP inhibitor can be determined.

Various factors can influence the actual effective amount used for a particular application. For example, the frequency of administration, duration of treatment, use of multiple cAMP inhibitors, route of administration, and severity of the liver condition may require an increase or decrease in the actual effective amount administered.

The frequency of administration can be any frequency that reduces abnormal cell growth or abnormal cell expansion in liver tissue of a mammal without producing significant toxicity to the mammal. For example, the frequency of administration can be from about four times a day to about once every other month, or from about once a day to about once a month, or from about one every other day to about once a week. In addition, the frequency of administration can remain constant or can be variable during the duration of treatment. As with the effective amount, various factors can influence the actual frequency of administration used for a particular application. For example, the effective amount, duration of treatment, use of multiple cAMP inhibitors, route of administration, and severity of the liver condition may require an increase or decrease in administration frequency.

An effective duration for cAMP inhibitor administration can be any duration that reduces abnormal cell growth or abnormal cell expansion in liver tissue of a mammal without producing significant toxicity to the mammal. Thus, the effective duration can vary from several days to several weeks, months, or years. In general, the effective duration for the treatment of a liver condition can range in duration from several days to several months. Once the cAMP administrations are stopped, however, a liver condition may return. Thus, the effective duration for preventing the return of a liver condition can be in some cases for as long as an individual mammal is alive.

Typically, an effective duration can range from about two months to about 36 months. Again, prophylactic treatments are typically longer in duration and can last throughout an individual mammal's lifetime.

Multiple factors can influence the actual effective duration used for a particular treatment or prevention regimen. For example, an effective duration can vary with the frequency of cAMP inhibitor administration, effective cAMP inhibitor amount, use of multiple cAMP inhibitors, route of administration, and severity of the liver condition.

A formulation containing a cAMP inhibitor can be in any form. For example, a formulation containing a cAMP inhibitor can be in the form of a solution or powder with or without a diluent to make an injectable suspension. In addition, the formulation can contain a cocktail of cAMP inhibitors. For example, a formulation can contain, without limitation, one, two, three, four, five, or more different cAMP inhibitors. Further, a formulation containing a cAMP inhibitor can contain additional ingredients including, without limitation, pharmaceutically acceptable vehicles, lactic acid, mannitol, sodium bicarbonate, and combinations thereof.

A pharmaceutically acceptable vehicle can be, for example, saline, water, lactic acid, and mannitol. In some cases, capsules or tablets can contain a cAMP inhibitor in enteric form. The dose supplied by each capsule or tablet can vary since an effective amount can be reached by administrating either one or multiple capsules or tablets. Any well known pharmaceutically acceptable material can be incorporated into a formulation containing a cAMP inhibitor including, without limitation, gelatin, cellulose, starch, sugar, or bentonite.

After administering a cAMP inhibitor to a mammal, the mammal can be monitored to determine whether or not a liver condition was treated. For example, a mammal can be assessed after treatment to determine whether or not the growth rate of a liver cyst was reduced (e.g., stopped). As described herein, any method can be used to assess growth rates.

The document will provide addition description in the following examples, which do not limit the scope of the invention described in the claims.

EXAMPLES

Example 1

Somatostatin Reduces cAMP Levels and Prevents Cyst Growth and Expansion

To determine whether cAMP plays a role in liver cystogenesis and whether the inhibition of this pathway prevents cyst growth and expansion, the following experiments were performed. The PCK rat, a spontaneous mutant derived from a colony of Crj:SD rats (Masyuk et al., *Am. J. Pathol.,* 165: 1719-1730 (2004)), was used. The PCK rat has renal and hepatic disease that resembles human ARPKD and is characterized by massive progressive cyst formation within kidney and the liver. Linkage and gene cloning analysis demonstrated that ARPKD and the cystic disease of the PCK rat are caused by mutations to orthologous genes, PKHD1/Pkhd1 (Ward et al., *Nat. Genet.,* 30:259-269 (2002)).

Methods and Materials
Isolating Bile Duct Explants

PCK rats (approximately 3 month old) were anesthetized with pentobarbital (50 mg/kg body weight, i.p.), the portal vein cannulated using PE-50 tubing, and blood flushed out with 0.9 percent sodium chloride. The liver was perfused with 150 mL of solution A (140 mM NaCl, 5,4 mM KCl, 0.8 mM $Na_2HPO_4$, 25 mM HEPES, pH 7.4) plus 0.5 mM etheylenglycol-bis (β-aminoethylether)-N,N'tetraacetic acid followed by 150 mL of solution A plus 5.0 mM $CaCl_2$ and 0.05 percent collagenase for 10 minutes at 37° C. The liver parenchymal cells were removed by a mechanical dissociation in solution A. The remaining clean portal tract residue was then placed in a 50-mL conical polypropylene centrifuge tube with 25 mL of RPMI 1640 medium, 8 mg of high-activity (type XI) collagenase (HAC), 10 mg of hyaluronidase, and 6 mg of DNase (Sigma Chemical Company, St. Louis, Mo.). The centrifuge tube was placed in a shaking water bath at 37° C. for 30 minutes. Macroscopic-sized pieces of portal tissue were allowed to sediment by unit gravity sedimentation, and the supernatant was discarded. This process was repeated 4 times.

Forming 3-D Cultures

The pelleted tissue fragments obtained in Example 1 were rapidly resuspended in 1.5 mL of neutralized rat-tail collagen (1.5 mg/mL, BD Biosciences) with 10 percent Matrigel (BD Biosciences) and then evenly spread over the surface of 22-mm wells of 12-well plates that were coated with 0.5 mL of the solidified rat-tail collagen mixture. Plates were placed in a tissue-culture incubator (37° C., 5% $CO_2$, and 100 percent % humidity) for 30 minutes until the collagen gel hardened. Then, 2 mL of warm cholangiocyte growth medium was added over the rat-tail collagen using a pipette, and the plates were returned to the incubator. The medium was changed every day.

Light Microscopic Examination of Cystic Structures

The bile duct explants formed cystic structures in 3-D culture that expand and grow over time. Micrographs of the same cystic structure were taken daily from day 1 to day 5. Using Image J software (NIH), the outer diameter of each cyst was determined from the average of two measurements at right angels, and the surface area of each cyst ($\pi D^2$) was calculated. The changes in rate of cyst growth and expansion were expressed as percent change from basal value (day 1).

Response to Somatostatin

To study the effect of somatostatin on cyst growth and expansion, somatostatin ($10^{-6}$M, Sigma) was added to each well twice a day from day 1 to day 5. The growth and expansion of cystic structure in response to somatostatin was compared to the rate of growth under basal conditions without somatostatin.

cAMP Measurements

Cystic structures were digested with colagenase (2 mg/mL, Sigma), rapidly frozen in liquid nitrogen, ground to a fine powder under liquid nitrogen in a stainless steel mortar, and homogenized in 10 volumes of cold 5% TCA in a glass-Teflon tissue grinder. After centrifugation at 600 g for 10 minutes, the supernatants were extracted with 3 volumes of water-saturated ether. The aqueous extracts were dried and reconstituted samples were processed using an enzyme ilmmiunoassay kit (Sigma, catalog # CA-201). Briefly, the ETA cyclic AMP kit is a competitive immunoassay for the quantitative determination of cyclic AMP in biological fluids and tissue. The kit uses a polyclonal antibody to cAMP to bind, in a competitive manner, the cAMP in the sample or an alkaline phosphatase molecule that has cAMP covalently attached to it. Samples or standards, alkaline phosphatase conjugates and antibodies are simultaneously incubated at room temperature in a secondary antibody coated microwell plate. The excess reagents are then washed away, and substrate is added. After a short incubation time, the enzyme reaction is stopped, and the yellow color generated read on a microplate reader at 405 nm. The intensity of the bound yellow color is inversely proportional to the concentration of cAMP in either standards or samples. The measured optical density is used to calculate the concentration of cAMP. The cAMP EIA may be used to assay cAMP samples from a wide range of sources. Samples diluted sufficiently (>1:10) can be read directly from the standard curve. Samples with very low levels of cAMP may be acetylated. Acetylation of the samples increases the sensitivity of the assay.

Results cAMP levels were significantly increased in bile ducts of the PCK rat as compared to the levels observed in bile ducts of normal rats (FIG. 1; P<0.01; n=7 for each group). In particular, cAMP levels were 146 percent higher in bile ducts from PCK rats as compared to the levels observed in bile ducts from normal rats. Thus, increased cAMP levels may play a role in liver cystogenesis.

Figure 2:
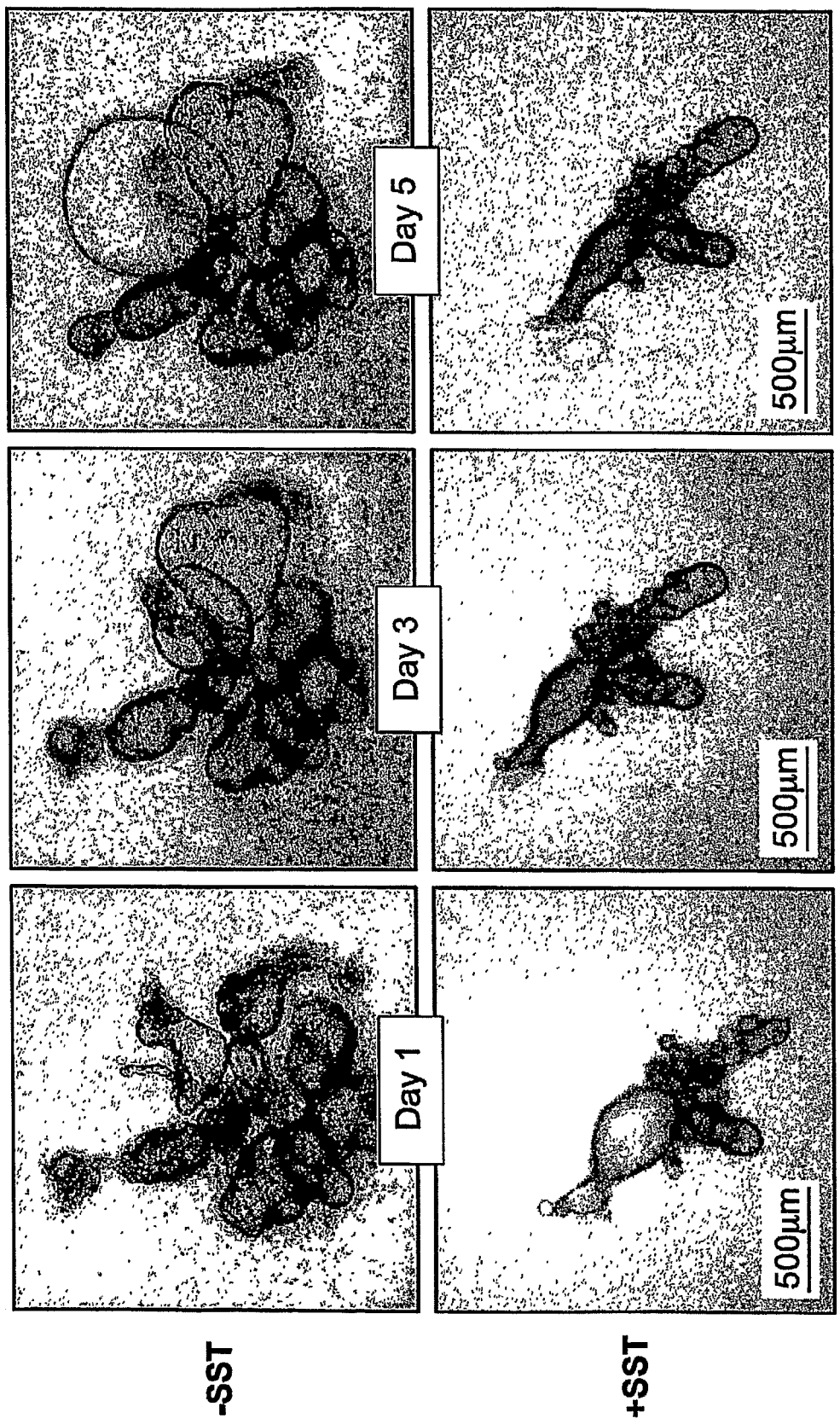
FIGS. 2 and 3 contain photographs of bile duct explants isolated from PCK (top panel) and normal (bottom panel) rats. They were grown in 3-D cultures with (+SST) or without (−SST) somatostatin for 1, 3, or 5 days.
Figure 3:
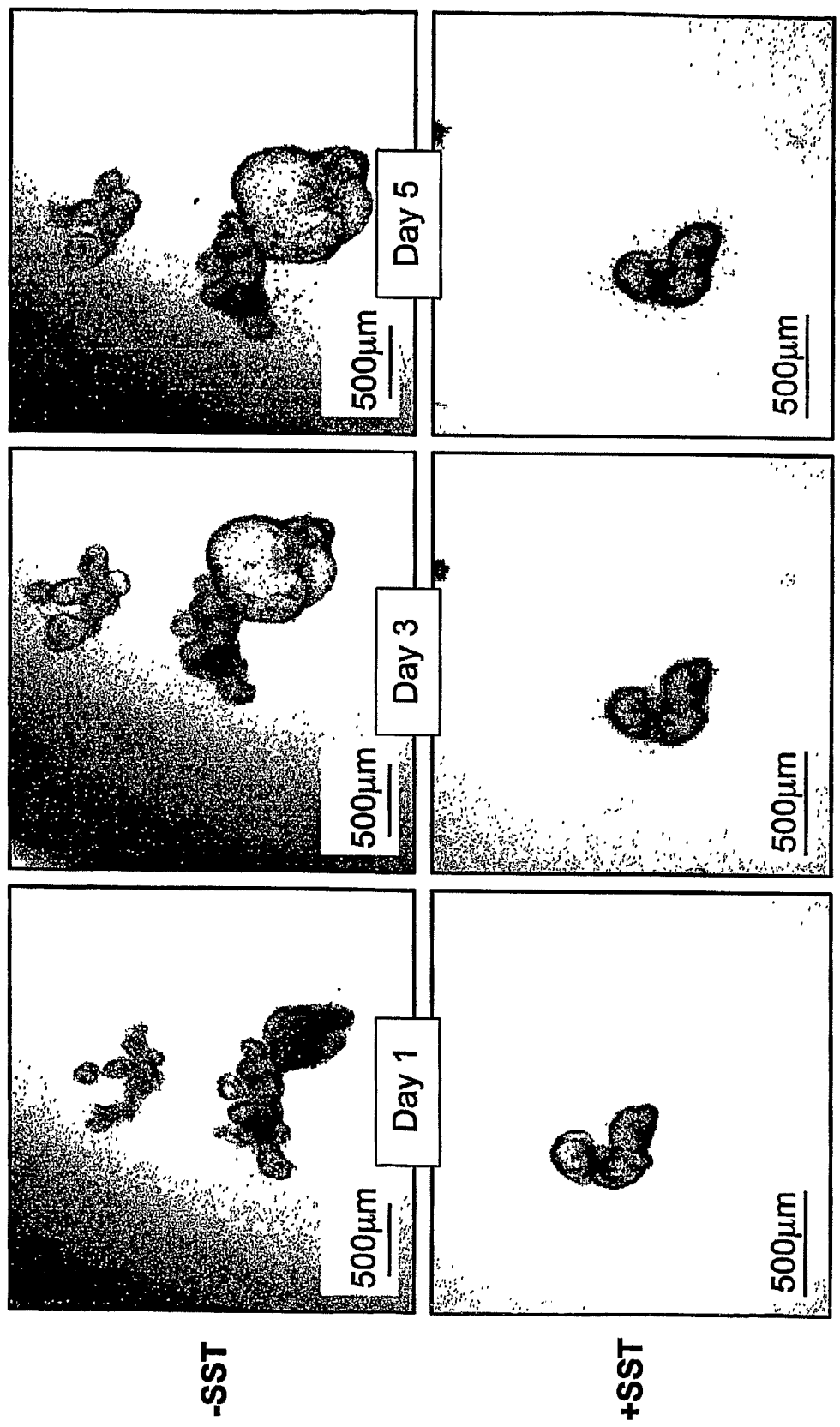
Figure 4A:
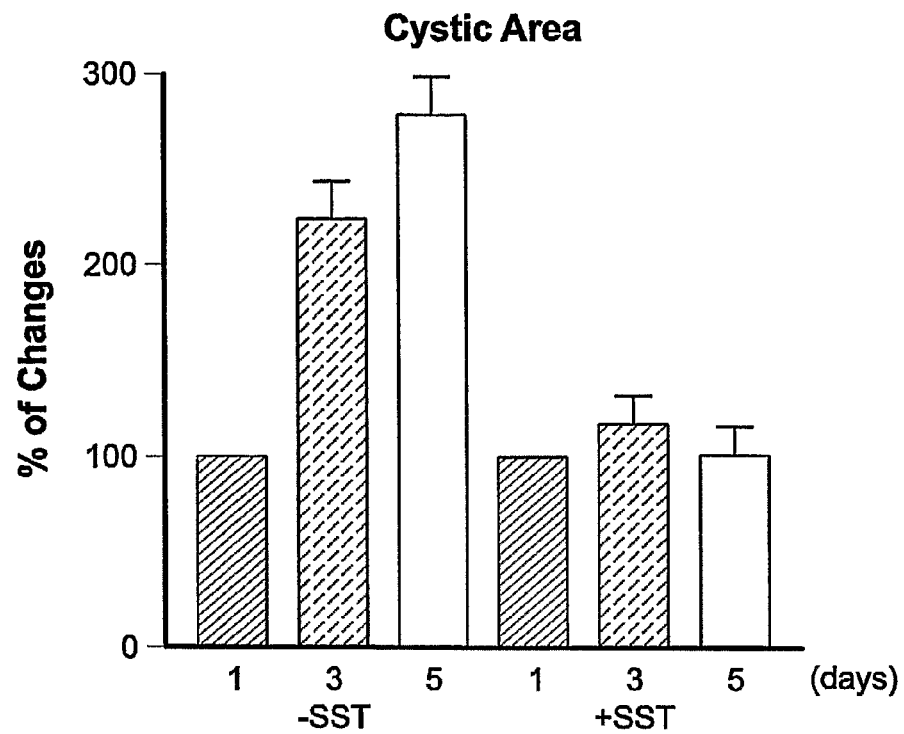
FIG. 4A is a graph plotting the percent change in cystic area measured in liver cysts from PCK rats treated with (+SST) or without (−SST) somatostatin for 1, 3, or 5 days.
Figure 4B:
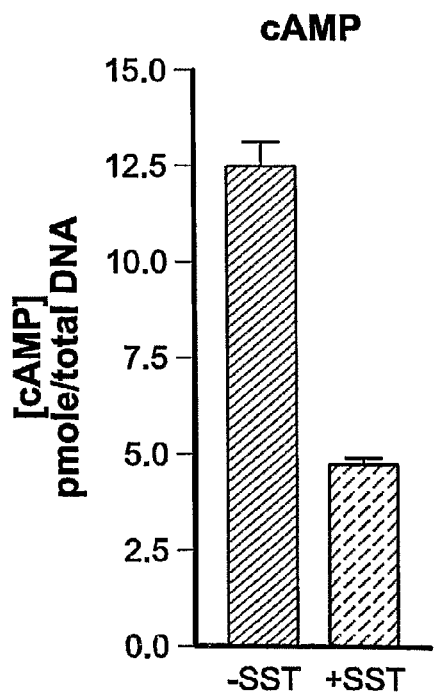
FIG. 4B is a graph plotting cAMP levels measured in liver cysts from PCK rats treated with (+SST) or without (−SST) somatostatin for 1, 3, or 5 days.

Somatostatin treatment prevented cyst growth and expansion of liver cysts isolated from PCK rats and grown in 3-D culture (FIGS. 2-4). Individual untreated cysts (n=223) from PCK rats exhibited growth and expansion in 3-D culture from day 1 to day 5, while individual somatostatin-treated cysts (N=188) did not exhibit growth and expansion in 3-D culture from day 1 to day 5 (FIGS. 2-3; p<0.001). In addition, the cystic area more than doubled from day 1 to day 5 for untreated cysts from PCK rats, while the cystic area for somatostatin-treated cysts remained relatively unchanged from day 1 to day 5 (FIG. 4).

Somatostatin treatment also reduced cAMP levels in liver cysts isolated from PCK rats and grown in 3-D culture (FIG. 4). In particular, liver cysts treated with somatostatin exhibited a cAMP level that was less than half that observed in untreated liver cysts.

Example 2

Somatostatin Reduces cAMP Levels and Prevents Cyst Growth and Expansion

Methods and Materials
Isolating Bile Ducts and Response to Somatostatin

Bile ducts were isolated from normal (n=15) and PCK (n=15) rats using a microdissection technique described previously (Roberts et al., *Proc. Natl. Acad. Sci.* USA 90:9080-4 (1993)). To study the effect of somatostatin oil cAMP concentration in bile ducts, isolated bile ducts were incubated with $10^{-7}$ M forskolin for 15 min. at 37° C. in the presence of 0.5 mM IBMX, an inhibitor of phosphodiesterases. Somatostatin ($10^{-6}$ M) was then added and the bile ducts were incubated for an additional 15 min. at 37° C.

3-D Culture and Response to Somatostatin

Bile ducts were suspended in 1.5 mL of type I rat tail collagen (1.5 mg/mL, BD Biosciences) supplemented with 10% Matrigel (BD Biosciences) and poured into a 35 mm dish that was pre-coated with 1 mL of the collagen mixture. The collagen gel was allowed to solidify for 20-30 min. at room temperature and was then overlaid with 1.5 mL of medium containing $10^{-7}$ M forskolin. The plates were incubated in a tissue culture incubator (37° C., 5% $CO_2$, and 100% humidity) in the presence or absence of somatostatin. Somatostatin ($10^{-6}$ M) was added to the medium every 12 hours. Development of cystic structures was assessed by light microscopy from day one to day five.

Measuring cAMP Concentration

The concentration of cAMP was measured in freshly isolated and cultured bile ducts and in serum. Serum was diluted 1:10 before assay. Cultured bile ducts were first released from the gel by adding 0.4 mL of high-activity type XI collagenase for 45 min. at 37° C. and washing twice with medium. cAMP concentrations were determined using the Bridge-It™ cAMP designer assay (Mediomics, LLC, St. Louis, Mo.). Results were expressed as pmol per μg of DNA. The amount of DNA in a single IBDU was determined using the DNeasy Tissue Kit (QIAGEN Inc., Valencia, Calif.).

Immunoblotting

Bile ducts grown in 3-D culture were released from the gel in three wells of a 6-well plate by adding 0.4 mL of high-activity type XI collagenase for 45 min. at 37° C. and washing twice with medium. The bile ducts were pooled, resuspended and sonicated in 0.25 M sucrose containing 0.01% soybean trypsin inhibitor (Worthington) and 0.1 mM phenylmethyl-sulfonyl fluoride. Each sample was solubilized, subjected to sodium dodecyl sulfate-polyacrylamide gel electrophoresis and transferred to a nitrocellulose membrane. After blocking non-specific binding, the membrane was incubated overnight at 4° C. with PCNA antibody (1:3000; Sigma-Aldrich) or SSTR2 antibody (1:100; Sigma). The membrane was then incubated with secondary antibodies conjugated to horseradish peroxidase (1:2000; Biosource) and bands were detected with the enhanced chemiluminescent plus detection system (Amersham).

Scanning Electron Microscopy

In preparation for scanning electron microscopy, livers were perfused for 5-10 min. with a solution of 4% paraformaldehyde and 2% glutaraldehyde in 0.1 M phosphate buffer (pH 7.4). Each liver was then cut into small pieces (about 2-4 $mm^3$) and immersed in 2% phosphate-buffered glutaraldehyde for two hours. Samples were postfixed in 1% osmium tetroxide for one hour, rinsed in distilled water, dehydrated in serial ethanol solutions, dried in a critical point dryer, sputter-coated with gold-palladium, and examined using a Hitachi 4700 Scanning Electron Microscope. Scanning electron micrographs were used to measure the lengths of cilia in bile ducts from normal and PCK rats as well as the areas of liver cysts (ImageJ, NIH Images).

Statistical Analysis

Values were expressed as mean±SEM, except for ciliary length, which was expressed as mean±SD. Statistical analysis was performed using the Student's t-test, and results were considered statistically significant at $p<0.05$.

Results

Figure 6:
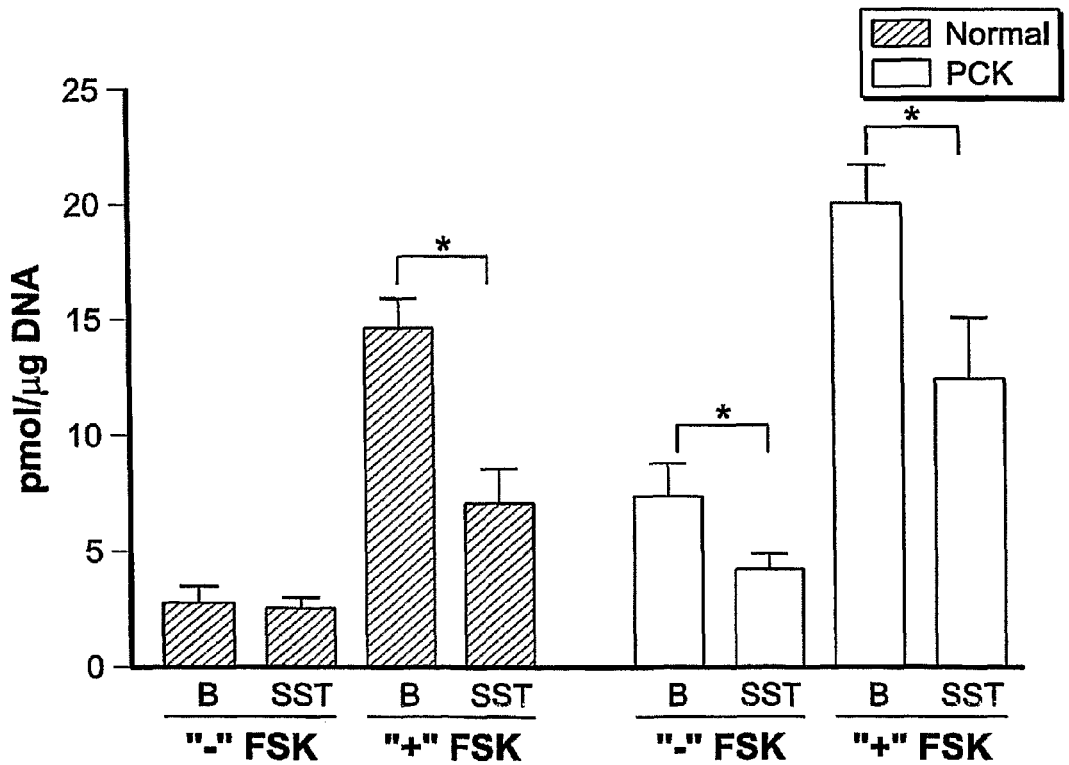
FIG. 6 is a graph plotting cAMP concentration in bile ducts from normal or PCK rats treated with somatostatin (SST; $10^{-6}$ M) or mock treated (B) in the presence or absence of forskolin (FSK; $10^{-7}$ M).
Figure 5:
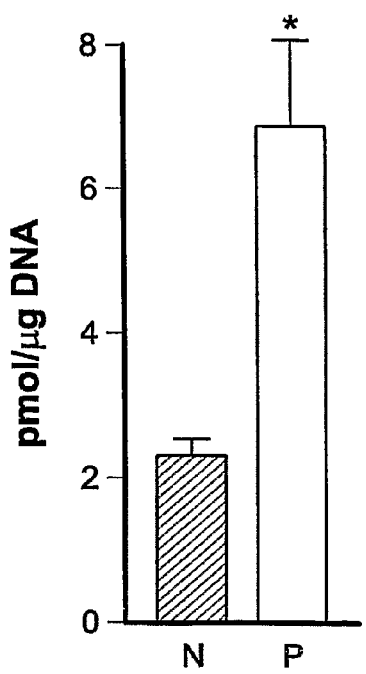
FIG. 5 is a graph plotting cAMP levels measured in bile ducts isolated from normal (N) or PCK (P) rats.

Analysis of freshly isolated bile ducts from normal and PCK rats indicated that the cAMP levels were significantly higher in cystic bile ducts than in normal bile ducts (FIG. 5). Somatostatin did not affect the basal level of cAMP in bile ducts from normal rats (FIG. 6, left panel, "−" FSK). hi bile ducts isolated from PCK rats, however, the cAMP concentration was reduced by 43% in the presence of somatostatin ($p<0.05$; FIG. 6). In bile ducts from normal and PCK rats, pretreatment with forskolin ($10^{-7}$ M) for 15 min. elevated the cAMP concentration. Subsequent addition of somatostatin ($10^{-6}$ M) for 15 min. decreased cAMP levels by 53% and 39% ($p<0.05$) in normal and cystic bile ducts, respectively (FIG. 6).

Figure 7A:
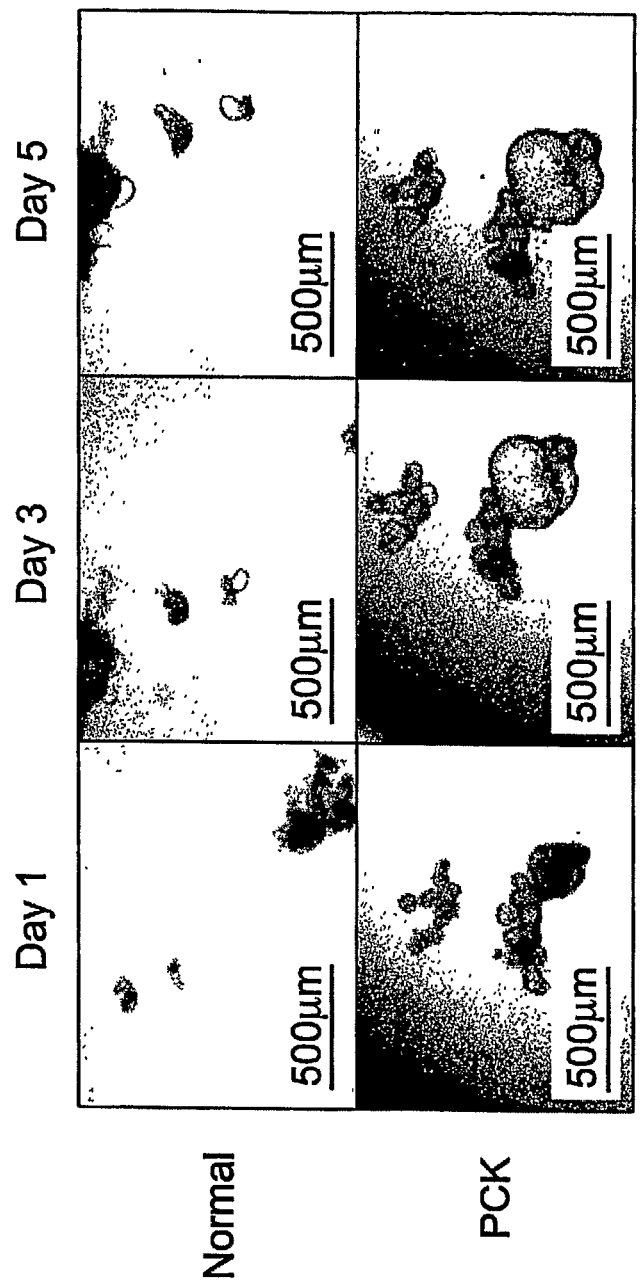
FIG. 7A contains photomicrographs of cystic structures formed by bile ducts that were isolated from normal or PCK rats and grown in 3-D culture for 1, 3, or 5 days.
Figure 7B:
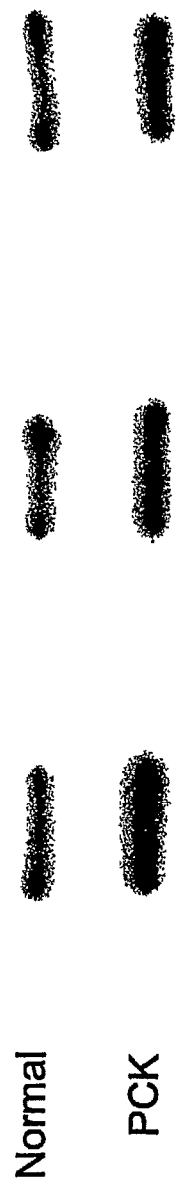
FIG. 7B contains a Western blot analyzing PCNA expression in normal and cystic bile ducts after 1, 3, or 5 days in 3-D culture.
Figure 8:
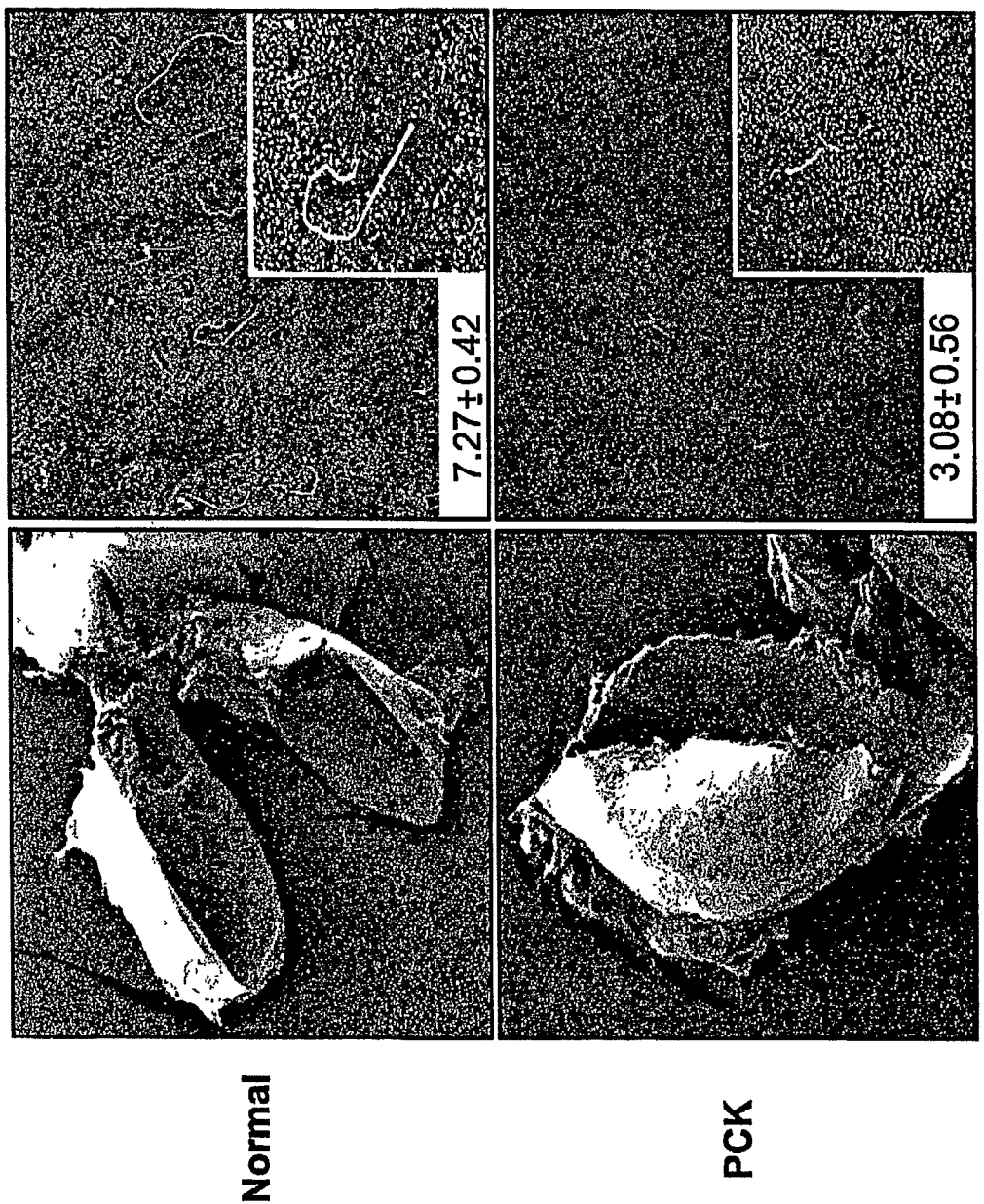
FIG. 8, left panels contain scanning electron micrographs of cysts formed in 3-D culture by bile ducts from normal and PCK rats. The right panels of FIG. 8 contain scanning electron micrographs of cilia in the bile ducts.

The effect of somatostatin on cyst growth and expansion during 3-D culture was examined. Bile ducts from normal and PCK rats, cultured between layers of collagen with 10% Matrigel, developed cystic structures that expanded over time (FIG. 7A). Analysis of PCNA expression indicated proliferation of cholangiocytes (FIG. 7B). Cystic bile ducts appeared to grow more rapidly than normal bile ducts. Importantly, bile ducts from the PCK rat grown in 3-D culture retained their in vivo morphology. As observed using SEM, the cilia in cystic bile ducts were much shorter than those in normal bile ducts (FIG. 8). These results are consistent with in vivo observations in the PCK rat (Masyuk et al., *Gastroenterology*, 125: 1303-10 (2003); Masyuk et al., *Am. J. Pathol.* 165:1719-30 (2004)).

Figure 9A:
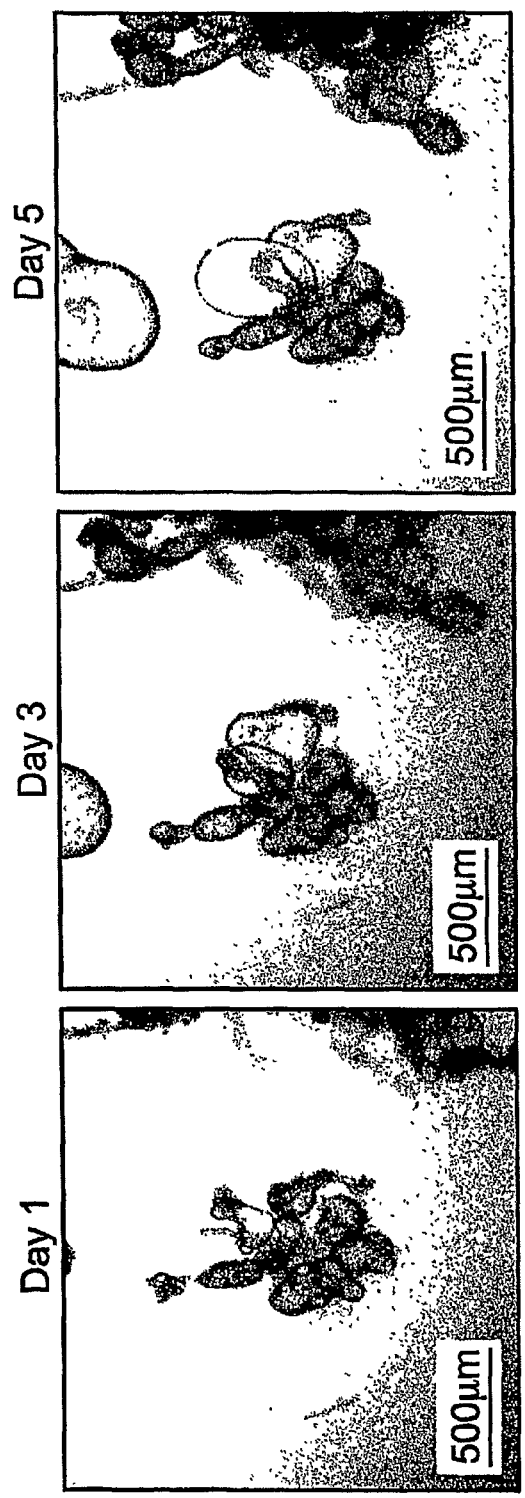
FIG. 9 contains photomicrographs of bile ducts that were isolated from PCK rats and maintained in 3-D culture for 1, 3, or 5 days in the absence (panel A) or presence (panel B) of somatostatin. Graphs plotting cystic areas and cAMP levels in the bile ducts are also presented.
Figure 9A:
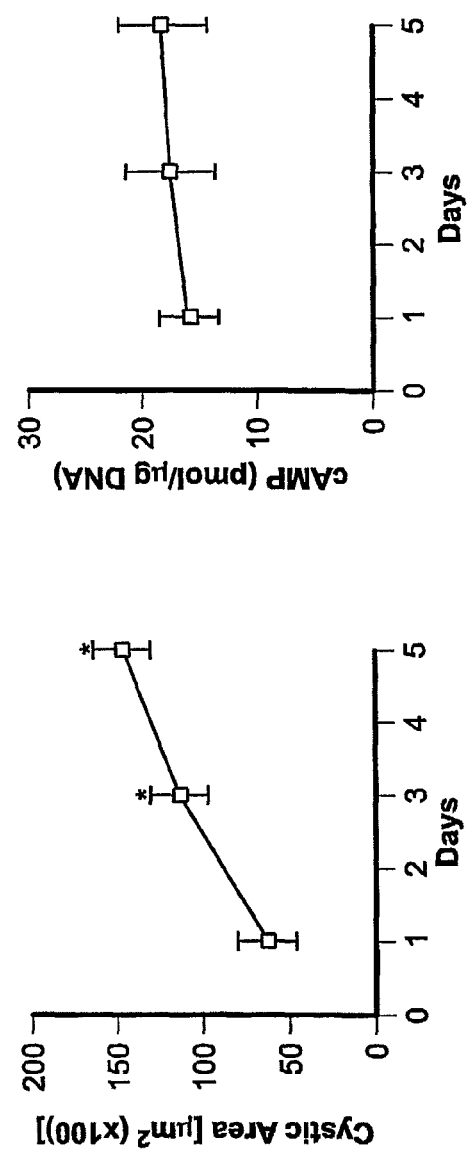
Figure 9B:
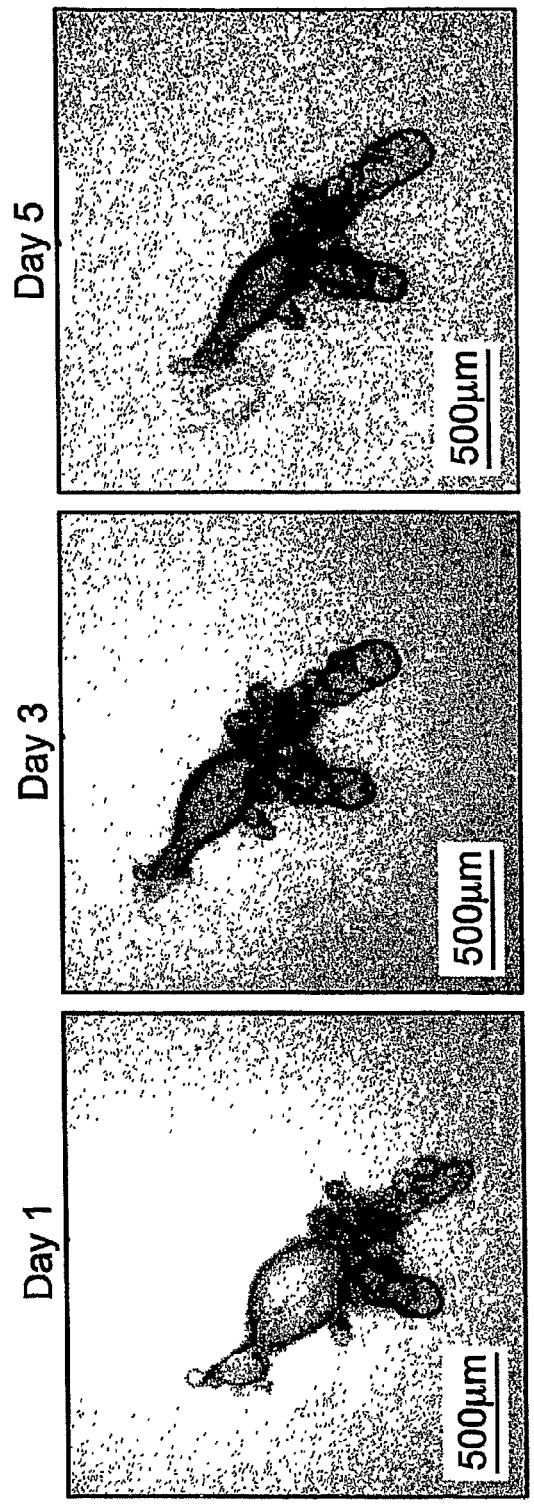
Figure 9B:
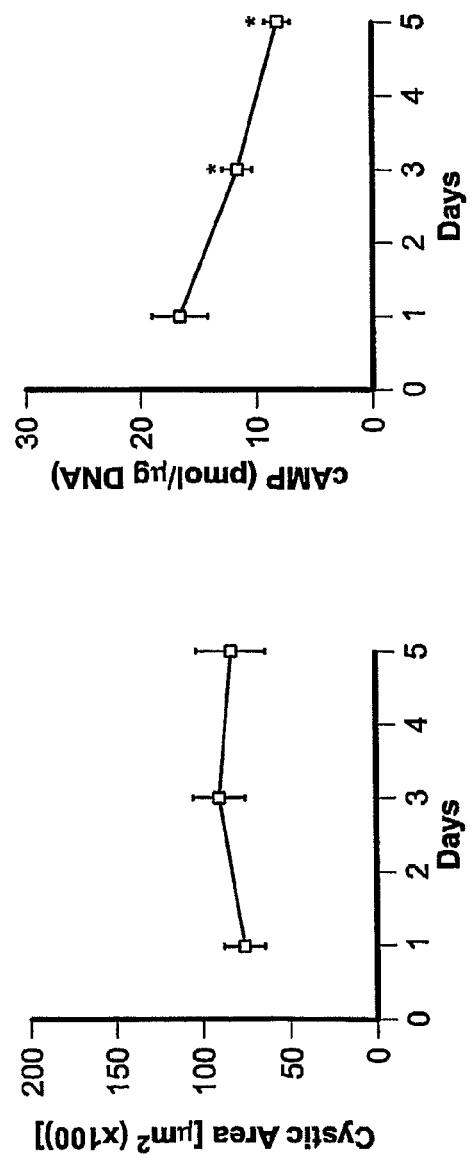

Changes in cystic area and cAMP level were examined in PCK bile ducts in the presence and absence of somatostatin. Bile ducts were treated with somatostatin ($10^{-6}$ M) every 12 hours for up to five days. In the absence of somatostatin, the cysts expanded over time while the levels of cAMP remained constant (FIG. 9A). In contrast, the cystic area did not change and the cAMP level was significantly reduced in the presence of somatostatin (FIG. 9B). In the absence of somatostatin, 76% of the bile ducts had an increased cystic area. In response to somatostatin treatment, the cystic area of 69% of the bile ducts was decreased, while the cystic area of only 8% of the bile ducts was increased.

These data suggest that: (i) the cAMP levels are markedly higher in bile ducts from PCK rats as compared to the cAMP levels in bile ducts from normal rats; (ii) somatostatin treatment significantly reduces cAMP concentration; and (iii) in the presence of somatostatin, the surface area of cysts formed by bile ducts from PCK rats in 3-D culture does not change over time.

Example 3

Using cAMP Modulating Agents to Treat Hepatic Polycystic Disease

Two groups of 24 three-week old PCK rats each are obtained for each cAMP modulating agent to be assessed in vivo. The rats of one group are untreated control rats that receive injections of saline, while the rats of the other group are treated with a particular cAMP modulating agent (10 mg/kg of body weight in saline). The cAMP modulating agent is somatostatin, octreotide, Sandostatin® LAR® (an injectable suspension of octreatide acetate that is a long-lasting formulation), lanreotide, Somatuline® SR® (a slow-release analog of lanreotide), vapreotide, or any other somatostatin analog, or ursodeoxycholic acid (e.g., ursodiol or UDCA), tauroursodeoxycholic acid (TUDCA), gastrin, or a combination thereof. Each rat receives its first injection at week zero and continues to receive injections twice daily for four, eight, or twelve weeks unless sacrificed earlier. Six rats from each group are sacrificed at four, eight, twelve, and sixteen weeks.

Once sacrificed, the rat's liver and kidney morphology is assessed using immunochistochemistry (IHC) and scanning electron microscopy (SEM). In addition, the number and size of liver cysts are assessed; the cAMP levels within liver tissue are measured; hepatic/renal functional tests (e.g., alkaline phosphatase, aspartate aminotransferase (AST), alanine aminotransferase (ALT), albumin, creatinine, protein total, bilirubin total, bilirubin direct, blood urea nitrogen (BUN) tests) are performed; and body, liver, and kidney weights are measured.

A reduction in the number and size of liver cysts for rats treated with a particular cAMP modulating agent can indicate that that cAMP modulating agent can be used to treat liver diseases such as hepatic polycystic disease.

Example 4

Octreotide Prevents Hepatic and Renal Cyst Progression and Fibrosis in vivo

Figure 10A:
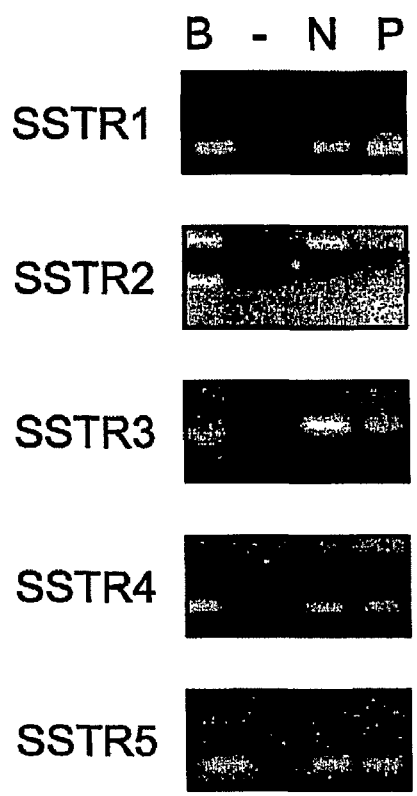
FIG. 10A contains images of gels separating RT-PCR products amplified using RNA from normal (N) or PCK (P) bile ducts and primers specific for SSTR1, SSTR2, SSTR3, SSTR4, and SSTR5. "B" refers to brain, which served as a positive control, and "−" indicates a negative control.
Figure 10B:
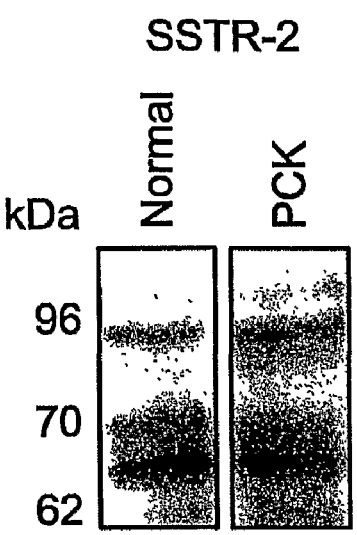
FIG. 10B contains a Western blot analyzing expression of SSTR2 polypeptides in bile ducts from normal and PCK rats.

Octreotide is a synthetic, metabolically stable somatostatin analog that binds to somatostatin receptor 2 (SSTR2) and SSTR5 with a high affinity and to SSTR3 with a low affinity (Froidevaux and Eberle, *Biopolymers*, 66:161-83 (2002)). The expression of all five SSTRs in cholangiocytes from the PCK rat was analyzed by RT-PCR, and the expression of SSR2, a major receptor for octreotide, was analyzed by Western blot. Expression of all five SSTRs was observed at the RNA level in cholangiocytes from the PCK rat, and expression of SSTR2 was observed at the protein level (FIG. 10).

Three week old PCK rats (n=60) were divided into five groups (three animals of each gender per treatment group). Each group was divided into two sub-groups. One sub-group was treated with saline while the second sub-group was treated with octreotide (Octreotide Acetate Injection; Novartis Pharma Stein AG, Switzerland). Groups 1, 2, 3, and 4 were treated with octreotide (10 µg/kg of body weight) for 4, 8, 12, and 16 weeks, respectively. Group 5 received a higher dose of octreotide, 100 µg/kg of body weight, for 4 weeks. Each animal was injected intraperitoneally every 12 hours. The octreotide dosage was adjusted to the animal weight twice a week. The control groups received an equal volume of saline.

At 4, 8, 12 and 16 weeks of age, animals were anesthetized with pentobarbital (50 mg/kg body weight, ip). Blood was collected by cardiac puncture for determination of hepatic and renal laboratory parameters and cAMP levels. Liver and kidney tissue sections (5 µm) were stained with hematoxylin-eosin and picrosirius red for analysis using light microscopy. Renal and hepatic fibrosis and cystic scores were measured using Meta-Morph software (Universal Imaging, West Chester, Pa., USA), a light microscope with a color digital camera (Nikon DXM 1200), and a Pentium IBM-compatible computer (Del OptiPlex). To measure the volume of a cyst or fibrosis, a colored threshold was applied at a level that allowed cystic tissue to be distinguished from non-cystic tissue and picrosirius red-positive stained fibrotic tissue to be distinguished from the background. The cystic and fibrotic scores were expressed as a percentage of total tissue.

Figure 11:
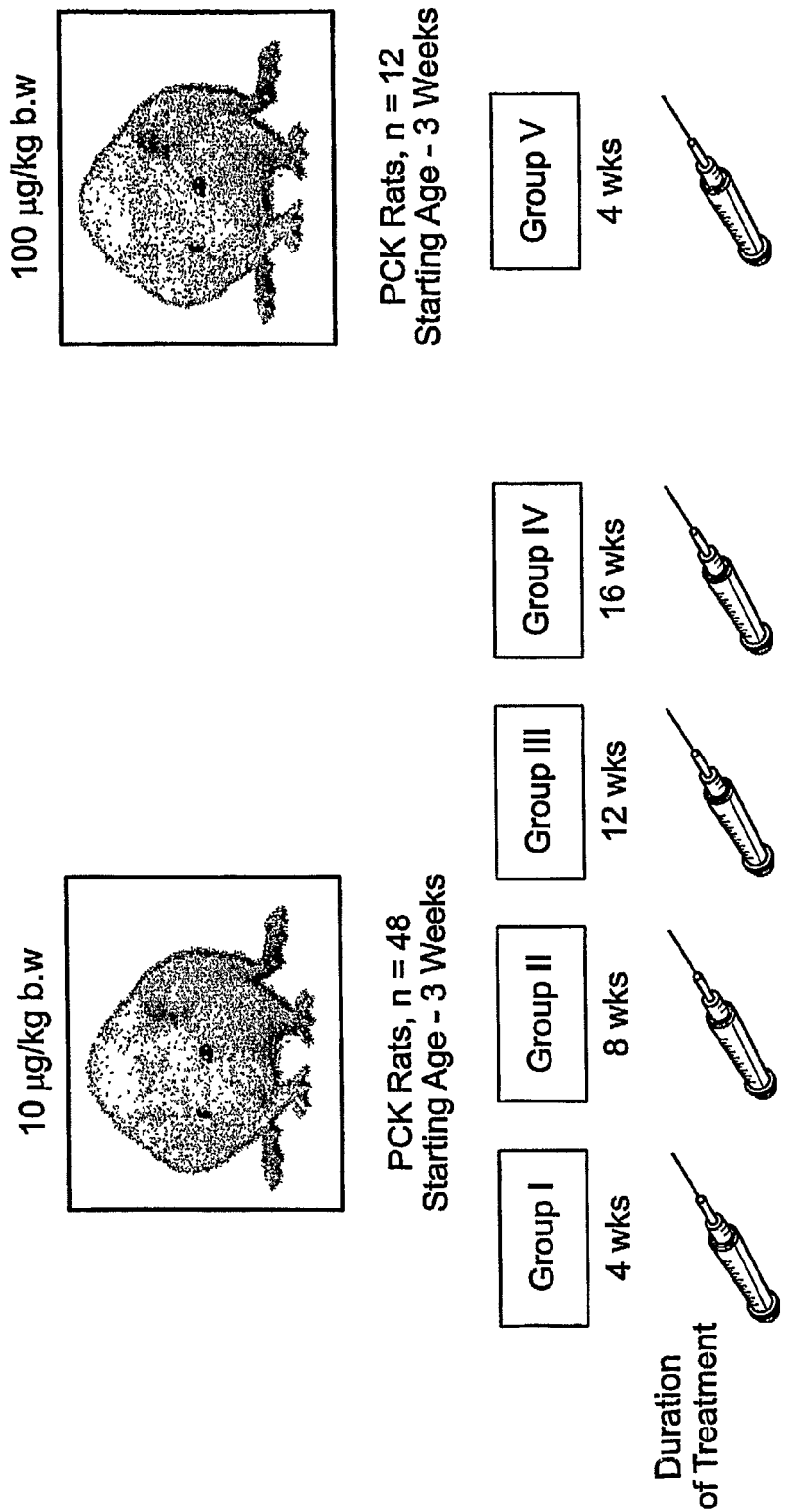
FIG. 11 is a schematic diagram illustrating the experimental design of animal studies investigating the effect of octreotide on hepatic and renal cyst progression and fibrosis in vivo.

After treating PCK rats with octreotide (FIG. 11), the following parameters were assessed: (i) body weight, (ii) hepatic and renal function, (iii) liver and kidney weight, (iv) cAMP levels in serum and freshly isolated bile ducts, (v) cystic score in liver and kidney; and (vi) fibrotic score in liver and kidney.

Octreotide did not affect hepatic or renal function at any dose administered. As presented in Table 1, none of the parameters assessed was observed to differ between octreotide-treated and saline-treated animals.

TABLE 1

Laboratory parameters in PCK rats treated with saline or octreotide.

| | Group I (4 weeks of treatment) | | Group II (8 weeks of treatment) | | Group III (12 weeks of treatment) | |
|---|---|---|---|---|---|---|
| | Saline | Octreotide (10 µg) | Saline | Octreotide (10 µg) | Saline | Octreotide (10 µg) |
| Alkaline Phosphatase (U/L): | | | | | | |
| Male | 248.5 ± 25.5 | 264.5 ± 41.5 | 317.0 ± 10.0 | 305.3 ± 20.4 | 225.0 ± 14.0 | 210.5 ± 24.5 |
| Female | 250.7 ± 11.7 | 238.5 ± 23.5 | 301.0 ± 10.0 | 258.7 ± 24.2 | 216.5 ± 26.5 | 237.0 ± 22.1 |
| Aspartate Aminotransferase (U/L): | | | | | | |
| Male | 204.5 ± 26.5 | 212.7 ± 41.1 | 233.1 ± 25.3 | 188.1 ± 20.6 | 185.8 ± 12.8 | 181.7 ± 39.2 |
| Female | 159.0 ± 24.3 | 135.0 ± 11.4 | 221.3 ± 28.5 | 211.2 ± 48.4 | 202.8 ± 4.8 | 207.5 ± 31.5 |
| Alanine Aminotransferase (U/L): | | | | | | |
| Male | 100.1 ± 19.4 | 114.3 ± 9.1 | 116.2 ± 8.4 | 102.2 ± 9.1 | 113.6 ± 11.7 | 102.8 ± 23.4 |
| Female | 90.5 ± 3.5 | 84.1 ± 6.3 | 99.3 ± 10.3 | 94.3 ± 14.8 | 109.5 ± 4.5 | 102.3 ± 12.2 |
| Albumin (g/dl): | | | | | | |
| Male | 3.36 ± 0.07 | 3.45 ± 0.15 | 3.3 | 2.97 ± 0.07 | 2.58 ± 0.03 | 2.55 ± 0.25 |
| Female | 3.56 ± 0.08 | 3.75 ± 0.05 | 3.35 ± 0.15 | 3.27 ± 0.09 | 2.93 ± 0.38 | 2.85 ± 0.05 |

TABLE 1-continued

Laboratory parameters in PCK rats treated with saline or octreotide.

|  |  |  |  |  | Group IV (16 weeks of treatment) | | HD (4 weeks of treatment) | |
| --- | --- | --- | --- | --- | --- | --- | --- | --- |
|  |  |  |  |  | Saline | Octreotide (10 µg) | Saline | Octreotide (100 µg) |
| Creatinine (mg/dl): | | | | | | | | |
| Male | 0.45 ± 0.04 | 0.49 ± 0.04 | 0.55 ± 0.05 | 0.6 | 0.6 | 0.6 | | |
| Female | 0.50 ± 0.01 | 0.55 ± 0.06 | 0.6 | 0.57 ± 0.03 | 0.6 | 0.6 | | |
| Protein total (g/dL): | | | | | | | | |
| Male | 5.30 ± 0.10 | 5.74 ± 0.19 | 5.4 ± 1.2 | 5.22 ± 1.4 | 5.3 ± 1.7 | 5.2 ± 0.03 | | |
| Female | 5.43 ± 0.15 | 5.70 ± 0.20 | 5.7 ± 1.6 | 5.53 ± 0.18 | 5.7 ± 0.3 | 5.2 ± 0.17 | | |
| Bilirubin Total (mg/dl): | | | | | | | | |
| Male | 0.15 ± 0.06 | 0.17 ± 0.0 | 0.2 | 0.2 | 0.3 | 0.3 | | |
| Female | 0.2 | 0.2 | 0.3 | 0.23 ± 0.03 | 0.2 | 0.2 | | |
| Bilirubin Direct (mg/dl): | | | | | | | | |
| Male | 0.1 | 0.1 | 0.1 | 0.1 | 0.1 | 0.1 | | |
| Female | 0.1 | 0.1 | 0.1 | 0.1 | 0.1 | 0.1 | | |
| Blood Urea Nitrogen (mg/dl): | | | | | | | | |
| Male | 15.7 ± 0.5 | 16.0 ± 0.6 | 17.5 ± 1.5 | 18.3 ± 1.6 | 21.2 ± 0.6 | 21.5 ± 1.5 | | |
| Female | 16.0 ± 0.6 | 16.7 ± 0.3 | 17.4 ± 1.3 | 15.7 ± 1.2 | 19.4 ± 2.3 | 20.5 ± 0.5 | | |
| Alkaline Phosphatase (U/L): | | | | | | | | |
| Male | | | | | 177.0 ± 17.3 | 189.5 ± 18.5 | 283.0 ± 12.8 | 276.8 ± 31.2 |
| Female | | | | | 160.5 ± 3.5 | 156.7 ± 4.3 | 275.3 ± 17.9 | 292.5 ± 14.3 |
| Aspartate Aminotransferase (U/L): | | | | | | | | |
| Male | | | | | 179.5 ± 58.5 | 145.1 ± 49.51 | 205.0 ± 10.2 | 191.0 ± 24.4 |
| Female | | | | | 169.0 ± 29.5 | 165.0 ± 36.46 | 179.8 ± 15.8 | 197.4 ± 25.7 |
| Alanine Aminotransferase (U/L): | | | | | | | | |
| Male | | | | | 102.5 ± 16.5 | 99.3 ± 17.6 | 107.3 ± 13.2 | 107.7 ± 13.1 |
| Female | | | | | 115.8 ± 10.6 | 112.7 ± 17.1 | 95.0 ± 1.41 | 91.3 ± 8.1 |
| Albumin (g/dl): | | | | | | | | |
| Male | | | | | 2.55 ± 0.05 | 2.47 ± 0.18 | 3.27 ± 0.14 | 3.23 ± 0.24 |
| Female | | | | | 2.84 ± 0.29 | 2.97 ± 0.09 | 3.25 ± 0.25 | 3.33 ± 0.13 |
| Creatinine (mg/dl): | | | | | | | | |
| Male | | | | | 0.57 ± 0.03 | 0.65 ± 0.05 | 0.5 | 0.5 |
| Female | | | | | 0.6 | 0.63 ± 0.03 | 0.6 | 0.6 |
| Protein total (g/dL): | | | | | | | | |
| Male | | | | | 5.1 ± 0.14 | 5.4 ± 0.35 | 5.5 ± 0.14 | 5.4 ± 0.15 |
| Female | | | | | 5.3 ± 0.16 | 5.6 ± 0.08 | 5.4 ± 0.42 | 5.3 ± 0.12 |
| Bilirubin Total (mg/dl): | | | | | | | | |
| Male | | | | | 0.2 | 0.2 | 0.2 | 0.2 |
| Female | | | | | 0.2 | 0.2 | 0.2 | 0.2 |
| Bilirubin Direct (mg/dl): | | | | | | | | |
| Male | | | | | 0.1 | 0.1 | 0.1 | 0.1 |
| Female | | | | | 0.1 | 0.1 | 0.1 | 0.1 |
| Blood Urea Nitrogen (mg/dl): | | | | | | | | |
| Male | | | | | 21.8 ± 1.35 | 20.3 ± 0.8 | 16.6 ± 1.14 | 17.1 ± 1.2 |
| Female | | | | | 22.5 ± 2.1 | 20.5 ± 0.9 | 16.5 ± 0.9 | 17.0 ± 2.6 |

Figure 12:
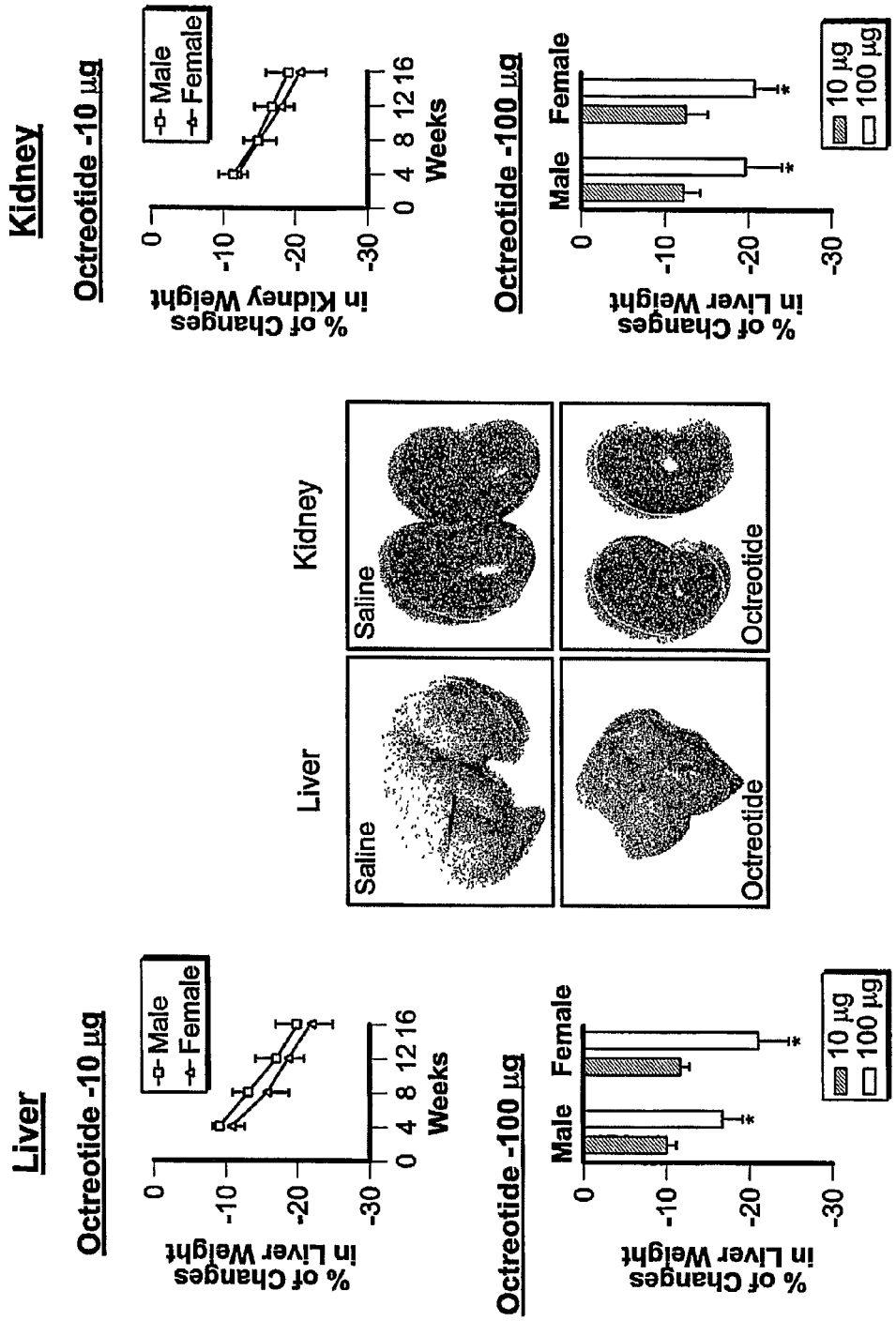
FIG. 12 contains graphs plotting the percent change in liver and kidney weight in male and female PCK rats after treatment with saline as compared to treatment with 10 μg/kg of octreotide for 4, 8, 12, or 16 weeks or 100 μg/kg of octreotide for 4 weeks. Representative images of liver and kidneys after 8 weeks of octreotide treatment are also presented.
Figure 13E:
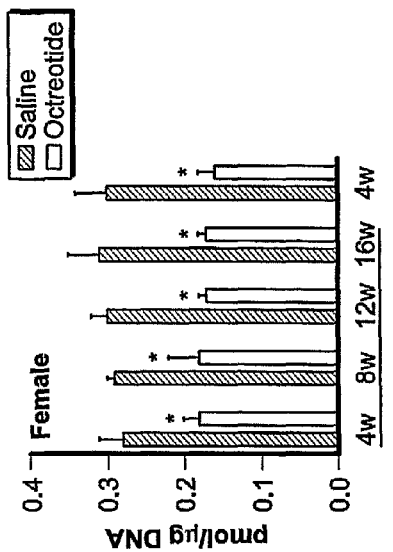
FIG. 13 contains graphs plotting cAMP levels in freshly isolated bile ducts (panels A-B) and serum (panels E-F) from PCK rats after treatment with saline as compared to treatment with 10 μg/kg of octreotide for 4, 8, 12, or 16 weeks or 100 μg/kg of octreotide for 4 weeks.
Figure 13F:
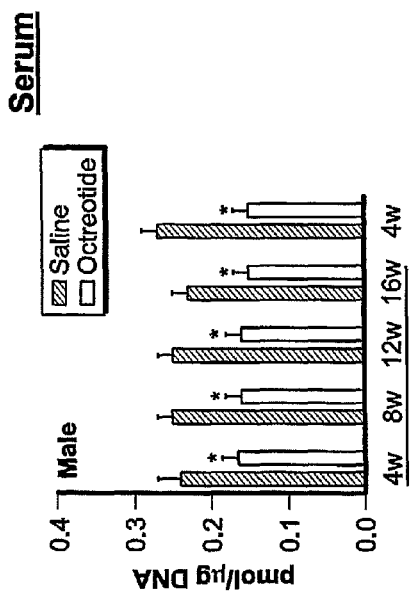
Figure 13G:
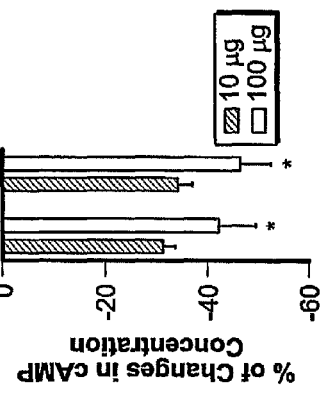
Figure 13H:
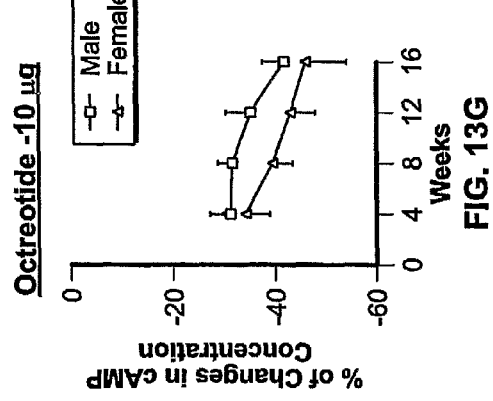
Figure 14:
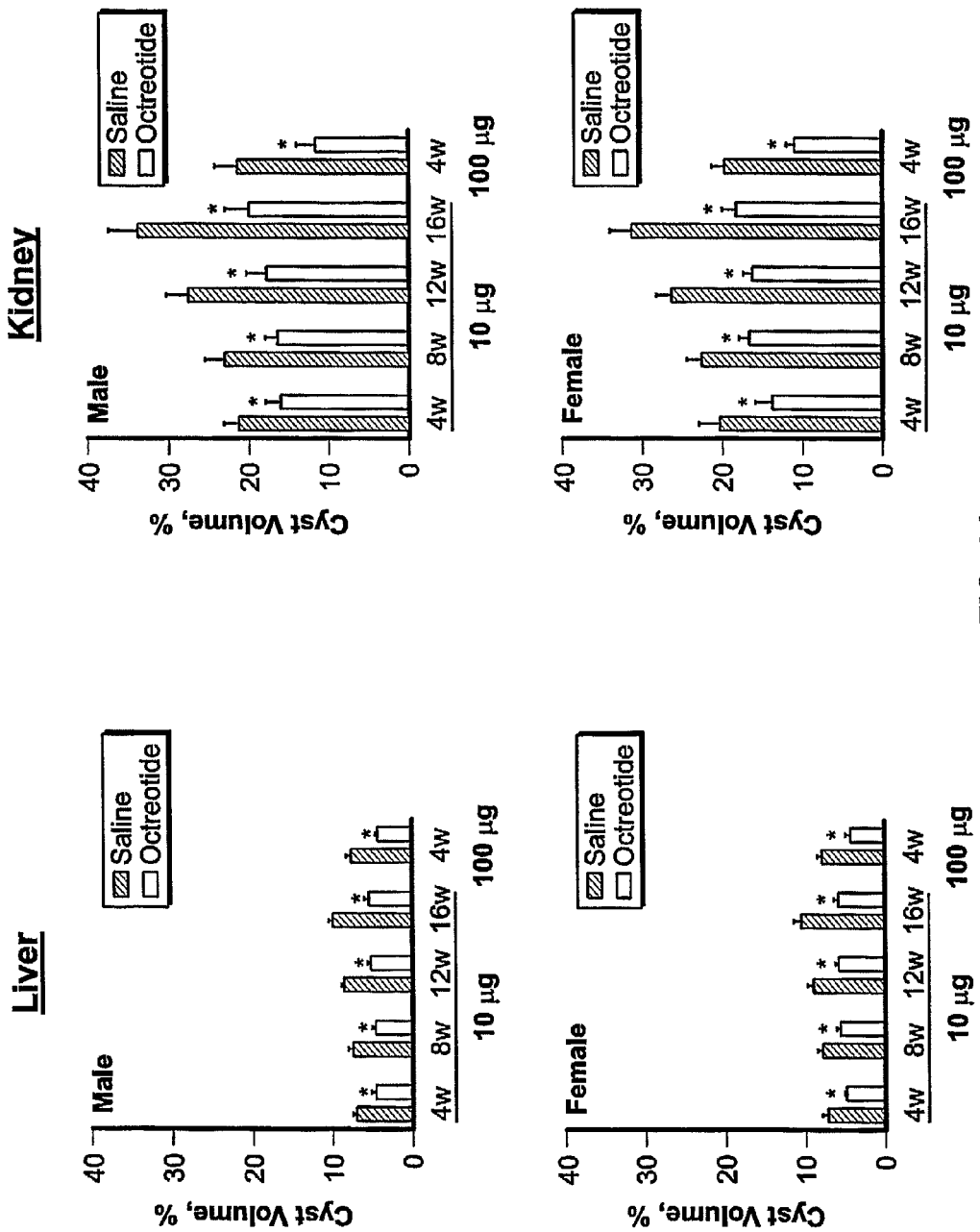
FIG. 14 contains graphs plotting cyst volume in liver and kidney of male and female PCI rats in response to treatment with saline, treatment with 10 µg/kg of octreotide for 4, 8, 12, or 16 weeks, or treatment with 100 µg/kg of octreotide for 4 weeks.
Figure 15:
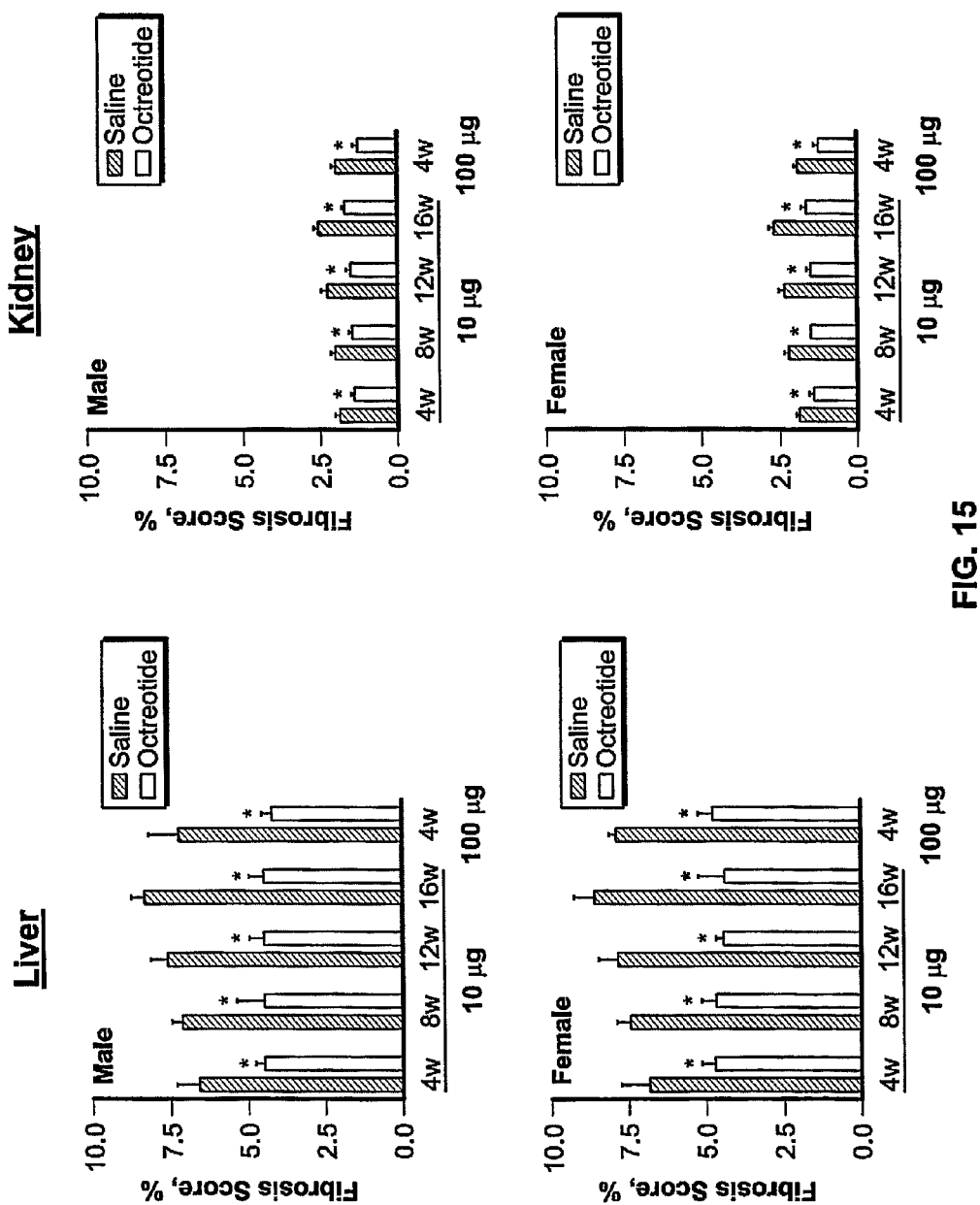
FIG. 15 contains graphs plotting hepatic and renal fibrosis scores in male and female PCK rats treated with saline, with 10 µg/kg of octreotide for 4, 8, 12, or 16 weeks, or with 100 µg/kg of octreotide for 4 weeks.
Figure 16:
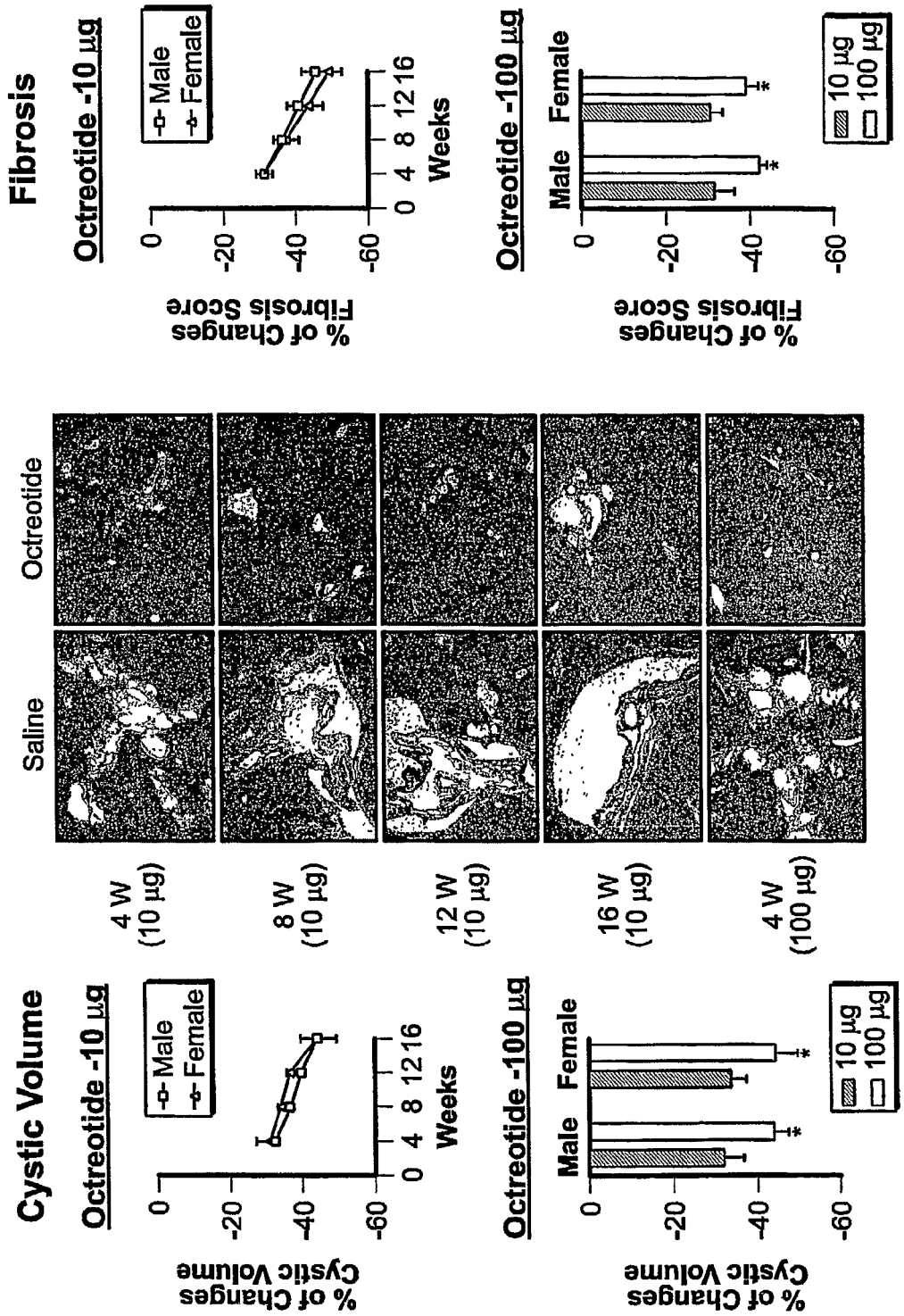
FIG. 16 contains graphs plotting the percent change in cystic volume or fibrosis score in the livers of PCK rats after treatment with saline as compared to treatment with 10 µg/kg of octreotide for 4, 8, 12, or 16 weeks or 100 µg/kg of octreotide for 4 weeks.
Figure 17:
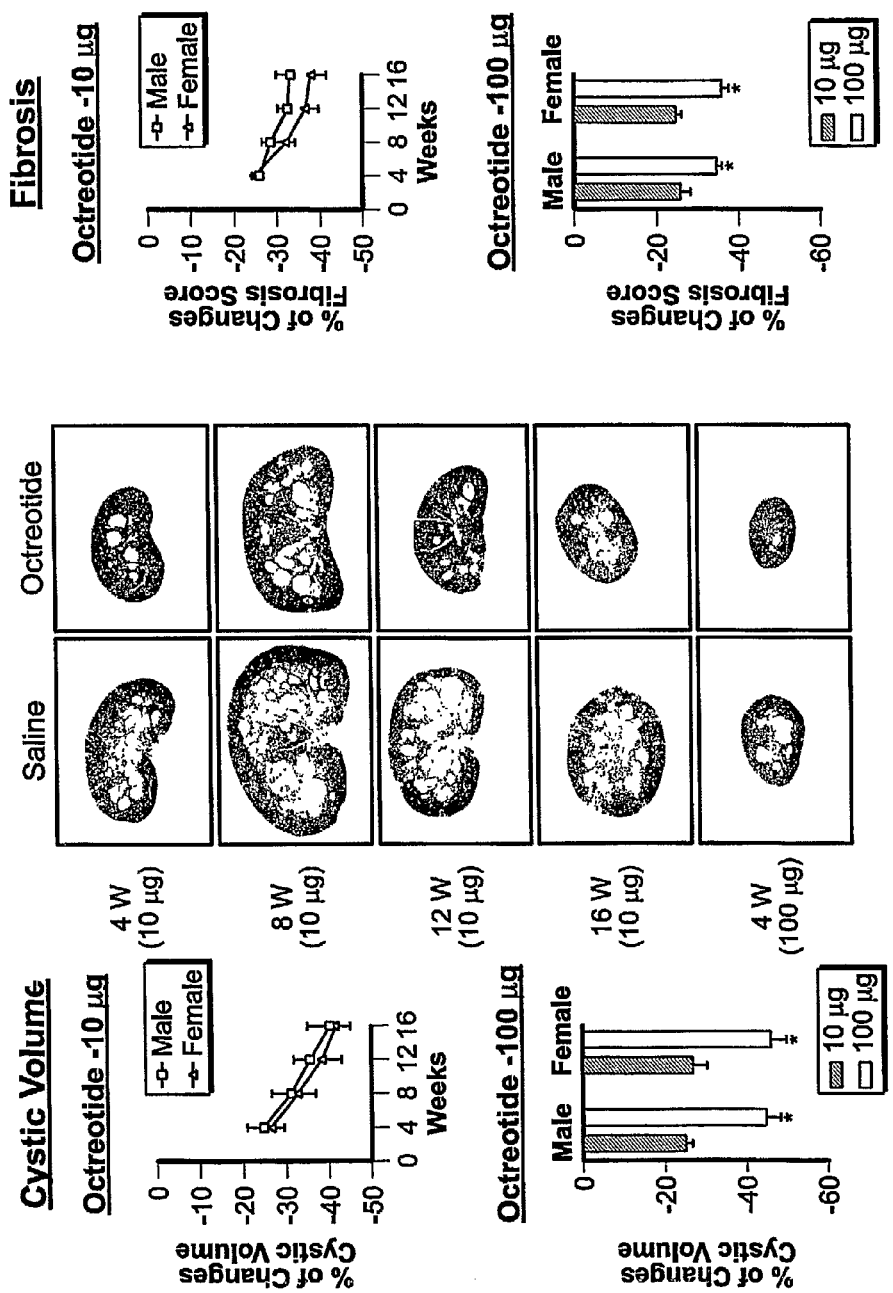
FIG. 17 contains graphs plotting the percent change in cystic volume or fibrosis score in the kidneys of PCK rats after treatment with saline as compared to treatment with 10 µg/kg of octreotide for 4, 8, 12, or 16 weeks or 100 µg/kg of octreotide for 4 weeks.

Body weights and weights of livers and kidneys from octreotide-treated and saline-treated PCK rats (males and females) are summarized in Table 2. No differences in body weight were observed between male or female PCK rats in the octreotide- and saline-treated groups. In contrast, liver and kidney weights were significantly decreased after octreotide treatment in each group studied. Moreover, liver and kidney weights declined progressively throughout the course of treatment. A more significant effect was observed in both organs at the higher dose of octreotide (FIG. 12).

cated that: (i) the volume of hepatic and renal cysts increased progressively over time in saline-treated male and female PCK rats (FIG. 14), (ii) hepatic and renal fibrosis did not change over time in saline-treated animals (FIG. 15), (iii) after administration of octreotide (10 µg/kg), the cystic volume in liver (FIGS. 14 and 16) and kidney FIGS. 14 and 17) decreased consistently and progressively, (iv) treatment with octreotide (10 µg/kg) resulted in a significant reduction in hepatic (FIGS. 15 and 16) and renal (FIGS. 15 and 17) fibrosis, and (iv) a higher dose of octreotide resulted in an even

TABLE 2

Body, liver and kidney weight in PCK rats treated with saline or octreotide.

| | Group 1 (4 weeks of treatment) | | Group II (8 weeks of treatment) | | Group III (12 weeks of treatment) | |
|---|---|---|---|---|---|---|
| | Saline | Octreotide (10 µg) | Saline | Octreotide (10 µg) | Saline | Octreotide (10 µg) |
| Body weight (g): | | | | | | |
| Male | 317.0 ± 7.1 | 299.7 ± 16.7 | 366.5 ± 77.1 | 347.7 ± 7.7 | 443.5 ± 4.95 | 430.7 ± 37.2 |
| Female | 219.0 ± 12.7 | 219.0 ± 16.5 | 277.5 ± 14.9 | 264.7 ± 15.3 | 291.7 ± 2.1 | 288.0 ± 2.8 |
| Liver weight (% body weight): | | | | | | |
| Male | 5.23 ± 0.13 | 4.76 ± 0.07* (↓9.0%) | 5.96 ± 0.21 | 5.24 ± 0.57* (↓12.8%) | 6.41 ± 0.23 | 5.31 ± 0.46* (↓17.2%) |
| Female | 5.98 ± 0.02 | 5.34 ± 0.24* (↓10.5%) | 6.38 ± 0.04 | 5.37 ± 0.22* (↓15.8%) | 6.82 ± 0.26 | 5.43 ± 0.24* (↓18.8%) |
| Kidney weight, (% body weight): | | | | | | |
| Male | 1.61 ± 0.08 | 1.43 ± 0.04* (↓11.2%) | 1.77 ± 0.04 | 1.52 ± 0.11* (↓14.6%) | 1.84 ± 0.16 | 1.53 ± 0.15* (↓16.8%) |
| Female | 1.49 ± 0.04 | 1.31 ± 0.04* (↓11.8%) | 1.59 ± 0.24 | 1.35 ± 0.06* (↓15.0%) | 1.73 ± 0.12 | 1.42 ± 0.11* (↓17.9%) |

| | Group IV (16 weeks of treatment) | | HD (4 weeks of treatment) | |
|---|---|---|---|---|
| | Saline | Octreotide (10 µg) | Saline | Octreotide (100 µg) |
| Body weight (g): | | | | |
| Male | 477.0 ± 29.7 | 439.7 ± 20.3 | 288.8 ± 29.6 | 259.0 ± 7.0 |
| Female | 313.0 ± 7.1 | 304.0 ± 12.5 | 186.8 ± 8.2 | 192.3 ± 3.8 |
| Liver weight (% body weight): | | | | |
| Male | 7.04 ± 0.11 | 5.64 ± 0.14* (↓19.9%) | 4.92 ± 0.45 | 4.18 ± 0.11* (↓15.1%) |
| Female | 7.20 ± 0.33 | 5.62 ± 0.25* (↓21.9%) | 5.81 ± 0.08 | 4.7 ± 0.35* (↓19.1%) |
| Kidney weight, (% body weight): | | | | |
| Male | 1.94 ± 0.09 | 1.57 ± 0.12* (↓18.9%) | 1.57 ± 0.12 | 1.27 ± 0.13* (↓19.3%) |
| Female | 1.86 ± 0.11 | 1.48 ± 0.13* (↓20.6%) | 1.41 ± 0.16 | 1.14 ± 0.07* (↓18.6%) |

Administration of octreotide lowered cAMP levels in freshly isolated bile ducts (FIG. 13, panels A-D) and in serum (FIG. 13, panels E-H). A longer duration of treatment with 10 µg/kg of octreotide resulted in a more significant reduction in the cAMP level in bile ducts (FIG. 13C) and serum (FIG. 13G). A higher dose of octreotide (100 µg/kg) decreased the cAMP concentration in bile duct (FIG. 13D) and serum (FIG. 13H) to an even greater extent.

The volumes of hepatic and renal cysts in the octreotide-treated and saline-treated PCK rats were determined, and the cysts were assessed for fibrosis (FIGS. 14-17). The data indicated that:

more significant reduction in cystic volume and fibrosis score in liver and kidney (FIG. 14-17).

These results indicated that octreotide treatment in the PCK rat (i) decreased liver and kidney weight, (ii) lowered the cAMP concentration, (iii) inhibited cystic volume and fibrosis in liver and kidney, and (iv) produced a more significant effect on all parameters analyzed at a higher dose. These results also demonstrated the effectiveness of octreotide for treatment of PCLD.

Example 5

Octreotide Therapy for PCLD in Humans

Figure 18:
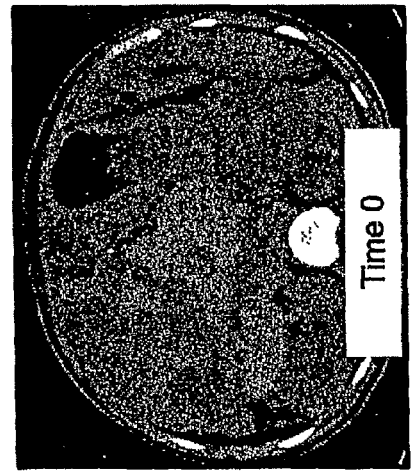
FIG. 18 contains images of the liver and kidneys of a patient with ADPKD and severe PCLD who was treated with octreotide-LAR for eight months.
Figure 18:
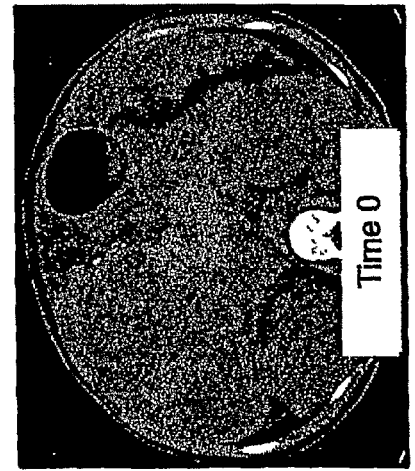
Figure 18:
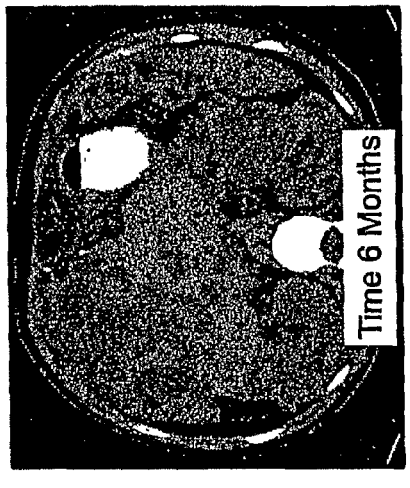
Figure 18:
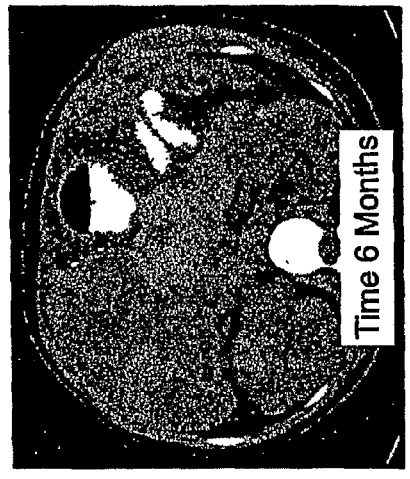

Octreotide-LAR was administered for eight months to a patient with autosomal dominant polycystic kidney disease and massive PCLD who developed ascites following a combined liver resection-cyst fenestration. Administration of octreotide-LAR reduced the need for paracenthesis and was accompanied by an 18% reduction in liver volume from 2,833 mL to 2,330 mL (FIG. 18) and a 12% reduction in kidney volume from 484 mL to 425 mL. These observations suggest that the somatostatin analogue octreotide decreases the rate of fluid secretion by the cystic epithelium following surgical fenestration of cysts.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for inhibiting cyst growth, said method comprising:
   (a) identifying liver tissue comprising a liver cyst, and
   (b) contacting said liver cyst with a cAMP inhibitor, wherein the cAMP inhibitor is somatostatin, ocetreotide, lanreotide, vapreotide, ursodeoxycholic acid, tauroursodeoxycholic acid or gastrin, under conditions wherein the growth rate of said liver cyst is reduced as compared to the growth rate of a comparable liver cyst not contacted with said cAMP inhibitor.

2. The method of claim 1, wherein said liver tissue is human liver tissue.

3. The method of claim 1, wherein said method comprises orally administering said cAMP inhibitor to said mammal.

4. The method of claim 1, wherein said method comprises injecting said cAMP inhibitor into said mammal.

5. The method of claim 1, wherein said method comprises detecting a reduced growth rate of said liver cyst following said contacting step.

6. A method for inhibiting cyst growth, said method comprising:
   (a) identifying liver tissue comprising a liver cyst having a growth rate, and
   (b) contacting said liver cyst with a cAMP inhibitor, wherein the cAMP inhibitor is somatostatin, ocetreotide, lanreotide, vapreotide, ursodeoxycholic acid, tauroursodeoxycholic acid or gastrin, under conditions wherein said growth rate of said liver cyst is reduced.

7. The method of claim 6, wherein said liver tissue is human liver tissue.

8. The method of claim 6, wherein said method comprises orally administering said cAMP inhibitor to said mammal.

9. The method of claim 6, wherein said method comprises injecting said cAMP inhibitor into said mammal.

10. The method of claim 6, wherein said method comprises detecting a reduced growth rate of said liver cyst following said contacting step.

11. A method for inhibiting cyst growth in a mammal, said method comprising:
    (a) identifying said mammal as having liver tissue comprising a liver cyst, wherein said liver cyst has a size, and
    (b) administering a cAMP inhibitor, wherein the cAMP inhibitor is somatostatin, ocetreotide, lanreotide, vapreotide, ursodeoxycholic acid, tauroursodeoxycholic acid or gastrin, to said mammal in an amount and at a frequency effective to prevent said size from increasing more than 100 percent within a two month time period.

12. The method of claim 11, wherein said mammal is a human.

13. The method of claim 11, wherein said cAMP inhibitor is formulated as a slow-release cAMP inhibitor.

14. The method of claim 11, wherein said administering step is effective to prevent said size from increasing more than 50 percent within a six month time period.

15. The method of claim 11, wherein said administering step is effective to prevent said size from increasing more than 25 percent within a six month time period.

16. The method of claim 11, wherein said administering step is effective to prevent said size from increasing more than 100 percent within a 12 month time period.

17. The method of claim 11, wherein said method comprises determining whether said size increased more than 100 percent within a 36 month time period.

* * * * *

UNITED STATES PATENT AND TRADEMARK OFFICE
CERTIFICATE OF CORRECTION

PATENT NO. : 8,232,241 B2
APPLICATION NO. : 11/915107
DATED : July 31, 2012
INVENTOR(S) : Nicholas F. LaRusso It is certified that error appears in the above-identified patent and that said Letters Patent is hereby corrected as shown below:

Title page, Column 2 (Other Publications), line 12, please delete "Didney" and insert --Kidney--, therefor.

In the Claims

Column 19, lines 31-32 (Claim 1), please delete "ocetreotide," and insert --octreotide,--, therefor.

Column 20, lines 6-7 (Claim 6), please delete "ocetreotide" and insert --octreotide,--, therefor.

Column 20, line 23 (Claim 11), please delete "ocetreotide," and insert --octreotide--, therefor.

Signed and Sealed this
Sixth Day of August, 2013

Teresa Stanek Rea
*Acting Director of the United States Patent and Trademark Office*